(12) United States Patent
Lei

(10) Patent No.: US 7,300,781 B2
(45) Date of Patent: Nov. 27, 2007

(54) **SITE-DIRECTED MUTAGENESIS OF *ESCHERICHIA COLI* PHYTASE**

(75) Inventor: Xingen Lei, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 317 days.

(21) Appl. No.: 11/018,709

(22) Filed: Dec. 20, 2004

(65) Prior Publication Data

US 2005/0095691 A1 May 5, 2005

Related U.S. Application Data

(62) Division of application No. 09/715,477, filed on Nov. 17, 2000, now Pat. No. 6,841,370.

(60) Provisional application No. 60/166,179, filed on Nov. 18, 1999.

(51) Int. Cl.
*C12N 9/16* (2006.01)
*C07H 21/04* (2006.01)

(52) U.S. Cl. .................. 435/196; 536/23.2

(58) Field of Classification Search .............. None
See application file for complete search history.

(56) References Cited

U.S. PATENT DOCUMENTS

| | | |
|---|---|---|
| 3,819,528 A | 6/1974 | Berry |
| 3,860,484 A | 1/1975 | O'Malley |
| 3,966,971 A | 6/1976 | Morehouse et al. |
| 4,038,140 A | 7/1977 | Jaworek et al. |
| 4,375,514 A | 3/1983 | Siewert et al. |
| 4,460,683 A | 7/1984 | Gloger et al. |
| 4,470,968 A | 9/1984 | Mitra et al. |
| 4,734,283 A | 3/1988 | Siren |
| 4,765,994 A | 8/1988 | Holmgren |
| 4,778,761 A | 10/1988 | Miyanohara et al. |
| 4,914,029 A | 4/1990 | Caransa et al. |
| 4,915,960 A | 4/1990 | Holmgren |
| 4,950,609 A | 8/1990 | Tischer et al. |
| 4,997,767 A | 3/1991 | Nozaki et al. |
| 5,024,941 A | 6/1991 | Maine et al. |
| 5,200,399 A | 4/1993 | Wettlaufer et al. |
| 5,268,273 A | 12/1993 | Buckholz |
| 5,290,765 A | 3/1994 | Wettlaufer et al. |
| 5,316,770 A | 5/1994 | Edwards, Jr. |
| 5,318,903 A | 6/1994 | Bewert et al. |
| 5,366,736 A | 11/1994 | Edwards, Jr. |
| 5,436,156 A | 7/1995 | Van Gorcom et al. |
| 5,443,979 A | 8/1995 | Vanderbeke et al. |
| 5,480,790 A | 1/1996 | Tischer et al. |
| 5,492,821 A | 2/1996 | Callstrom et al. |
| 5,516,525 A | 5/1996 | Edwards, Jr. |
| 5,554,399 A | 9/1996 | Vanderbeke et al. |
| 5,556,771 A | 9/1996 | Shen et al. |
| 5,593,963 A | 1/1997 | Van Ooijen et al. |
| 5,612,055 A | 3/1997 | Bedford et al. |
| 5,691,154 A | 11/1997 | Callstrom et al. |
| 5,716,655 A | 2/1998 | Hamstra et al. |
| 5,736,625 A | 4/1998 | Callstrom et al. |
| 5,780,292 A | 7/1998 | Nevalainen et al. |
| 5,827,709 A | 10/1998 | Barendse et al. |
| 5,830,696 A | 11/1998 | Short |
| 5,830,733 A | 11/1998 | Nevalainen et al. |
| 5,834,286 A | 11/1998 | Nevalainen et al. |
| 5,853,779 A | 12/1998 | Takebe et al. |
| 5,863,533 A | 1/1999 | VanGorcom et al. |
| 5,876,997 A | 3/1999 | Kretz |
| 5,891,708 A | 4/1999 | Saniez et al. |
| 5,900,525 A | 5/1999 | Austin-Phillips et al. |
| 5,902,615 A | 5/1999 | Saniez et al. |
| 5,935,624 A | 8/1999 | DeLuca et al. |
| 5,955,448 A | 9/1999 | Colaco et al. |
| 5,972,669 A | 10/1999 | Harz et al. |
| 5,985,605 A | 11/1999 | Cheng et al. |
| 5,989,600 A | 11/1999 | Nielsen et al. |
| 6,022,555 A | 2/2000 | DeLuca et al. |
| 6,039,942 A | 3/2000 | Lassen et al. |
| 6,063,431 A | 5/2000 | Bae et al. |
| 6,083,541 A | 7/2000 | Hamstra et al. |
| 6,110,719 A | 8/2000 | Kretz |
| 6,139,892 A | 10/2000 | Fredlund et al. |
| 6,139,902 A | 10/2000 | Kondo et al. |
| 6,140,077 A | 10/2000 | Nakamura et al. |
| 6,183,740 B1 | 2/2001 | Short et al. |
| 6,190,897 B1 | 2/2001 | Kretz |

(Continued)

FOREIGN PATENT DOCUMENTS

CN     1126243 A     7/1996

(Continued)

OTHER PUBLICATIONS

Dassa et al., "Identification of the Gene *appA* for the Acid Phosphatase (pH Optimum 2.5) of *Escherichia coli*," *Mol. Gen. Genet.*, 200:68-73 (1985).

(Continued)

*Primary Examiner*—Elizabeth Slobodyansky
(74) *Attorney, Agent, or Firm*—Nixon Peabody LLP

(57) ABSTRACT

The present invention relates to an isolated mutant acid phosphatase/phytase with improved enzymatic properties. The mutant acid phosphatase/phytase composition is particularly useful in animal feed compositions.

10 Claims, 4 Drawing Sheets

U.S. PATENT DOCUMENTS

| | | | |
|---|---|---|---|
| 6,204,012 | B1 | 3/2001 | Hellmuth et al. |
| 6,248,938 | B1 | 6/2001 | Austin-Phillips et al. |
| 6,261,592 | B1 | 7/2001 | Nagashima et al. |
| 6,264,946 | B1 | 7/2001 | Mullertz et al. |
| 6,274,178 | B1 | 8/2001 | Beven et al. |
| 6,277,623 | B1 | 8/2001 | Oh et al. |
| 6,284,502 | B1 | 9/2001 | Maenz et al. |
| 6,291,221 | B1 | 9/2001 | van Loon et al. |
| 6,309,870 | B1 | 10/2001 | Kondo et al. |
| 6,350,602 | B1 | 2/2002 | Van Gorcom et al. |
| 6,391,605 | B1 | 5/2002 | Kostrewa et al. |
| 6,451,572 | B1 | 9/2002 | Lei |
| 6,475,762 | B1 | 11/2002 | Stafford et al. |
| 6,511,699 | B1 | 1/2003 | Lei |
| 6,514,495 | B1 | 2/2003 | Svendsen et al. |
| 6,599,735 | B1 | 7/2003 | Bartók et al. |
| 6,720,174 | B1 | 4/2004 | Lehmann |
| 6,841,370 | B1 | 1/2005 | Lei |
| 6,974,690 | B2 | 12/2005 | Lei |
| 7,022,371 | B2 | 4/2006 | Stafford et al. |
| 7,026,150 | B2 | 4/2006 | Lei |
| 2001/0018197 | A1 | 8/2001 | Wong et al. |
| 2001/0029042 | A1 | 10/2001 | Fouache et al. |
| 2002/0068350 | A1 | 6/2002 | Kondo et al. |
| 2002/0102692 | A1 | 8/2002 | LEI |
| 2002/0127218 | A1 | 9/2002 | Svendsen et al. |
| 2002/0136754 | A1 | 9/2002 | Short et al. |
| 2003/0092155 | A1 | 5/2003 | Kostrewa et al. |
| 2003/0206913 | A1 | 11/2003 | Webel et al. |
| 2004/0126844 | A1 | 7/2004 | Lei et al. |
| 2006/0153902 | A1 | 7/2006 | Lei |

FOREIGN PATENT DOCUMENTS

| | | |
|---|---|---|
| EP | 0 420 358 A1 | 4/1991 |
| EP | 0 449 376 A2 | 10/1991 |
| EP | 0 556 883 A1 | 8/1993 |
| EP | 0 649 600 A1 | 4/1995 |
| EP | 0 684 313 A2 | 11/1995 |
| EP | 0 699 762 A2 | 3/1996 |
| EP | 0 772 978 B1 | 5/1997 |
| EP | 0 779 037 A1 | 6/1997 |
| EP | 0 897 010 A2 | 2/1999 |
| EP | 0 897 985 A2 | 2/1999 |
| EP | 0 909 821 A1 | 4/1999 |
| EP | 0 925 723 A1 | 6/1999 |
| EP | 0 955 362 A1 | 11/1999 |
| EP | 0 960 934 A1 | 12/1999 |
| GB | 2 286 396 A | 8/1995 |
| GB | 2 316 082 A | 2/1998 |
| JP | 10-276789 | 10/1998 |
| RU | 2 113 468 C1 | 6/1998 |
| WO | WO 86/01179 A1 | 2/1986 |
| WO | WO 90/03431 A1 | 4/1990 |
| WO | WO 90/05182 A1 | 5/1990 |
| WO | WO 91/05053 A1 | 4/1991 |
| WO | WO 91/14773 A2 | 10/1991 |
| WO | WO91/14782 | 10/1991 |
| WO | WO 93/14645 A1 | 8/1993 |
| WO | WO 93/16175 A1 | 8/1993 |
| WO | WO 93/19759 A1 | 10/1993 |
| WO | WO94/03072 | 2/1994 |
| WO | WO94/03612 | 2/1994 |
| WO | WO 91/16076 A1 | 5/1997 |
| WO | WO97/35017 | 9/1997 |
| WO | WO 97/39638 A1 | 10/1997 |
| WO | WO 97/45009 A2 | 12/1997 |
| WO | WO97/48812 | 12/1997 |
| WO | WO98/05785 | 2/1998 |
| WO | WO 98/06856 A1 | 2/1998 |
| WO | WO98/20139 | 5/1998 |
| WO | WO 98/30681 A1 | 7/1998 |
| WO | WO 98/44125 A1 | 10/1998 |
| WO | WO 98/54980 A2 | 12/1998 |
| WO | WO99/08539 | 2/1999 |
| WO | WO 99/49022 A1 | 9/1999 |
| WO | WO 99/49740 A1 | 10/1999 |
| WO | WO 00/10404 A2 | 3/2000 |
| WO | WO 00/20569 A1 | 4/2000 |
| WO | WO 00/41509 A2 | 7/2000 |
| WO | WO 00/43503 A1 | 7/2000 |
| WO | WO 00/47060 A1 | 8/2000 |
| WO | WO 00/58481 A2 | 10/2000 |
| WO | WO 00/71728 A1 | 11/2000 |
| WO | WO 00/72700 A1 | 12/2000 |
| WO | WO 01/36607 A1 | 5/2001 |
| WO | WO 01/58275 A2 | 8/2001 |
| WO | WO 01/58276 A2 | 8/2001 |

OTHER PUBLICATIONS

Granovskii et al., "Expression of Hepatitis B Virus HBsAg Gene in Yeast Cells Under Control of Promotor Region of PHO5 Gene," *Soviet Progress in Virology* 5:45-47 (1985).

Touati et al., "Pleiotropic Mutations in *appR* Reduce pH 2.5 Acid Phosphatase Expression and Restore Succinate Utilisation in CRP-deficient Strains of *Escherichia coli*," *Mol. Gen. Genet.* 202:257-264 (1986).

Sidhu et al., "Analysis of α-Factor Secretion Signals by Fusing with Acid Phosphatase of Yeast," *Gene* 54:175-184 (1987).

Zvonok et al., "Construction of Versatile *Escherichia coli*-Yeast Shuttle Vectors for Promoter Testing in *Saccharomyces cerevisiae*," *Gene* 66(2):313-318 (1988).

Dassa et al., "The Complete Nucleotide Sequence of the *Escherichia coli* Gene *appA* Reveals Significant Homology Between pH 2.5 Acid Phosphatase and Glucose-1-Phosphatase," *Journal of Bacteriology* 172(9):5497-5500 (1990).

Ostanin et al., "Overexpression, Site-Directed Mutagenesis, and Mechanism of *Escherichia coli* Acid Phosphatase," *Journal of Biological Chemistry* 267(32):22830-22836 (1992).

Ostanin et al., "Asp$^{304}$ of *Escherichia coli* Acid Phosphatase is Involved in Leaving Group Protonation," *J. of Biol. Chem.* 268(28):20778-20784 (1993).

Piddington et al., "The Cloning and Sequencing of the Genes Encoding Phytase (*phy*) and pH 2.5-Optimum Acid Phosphatase (*aph*) from *Aspergillus niger* var. *awamori*," *Gene* 133:55-62 (1993).

Blondeau et al., "Development of High-Cell-Density Fermentation for Heterologous Interleukin Iβ Production in *Kluyveromyces lactis* Controlled by the PHO5 Promoter," *Appl. Microbiol Biotechnol.* 41:324-329 (1994).

Moore et al., "Molecular Cloning, Expression and Evaluation of Phosphohydrolases for Phytate-Degrading Activity," *Journal of Industrial Microbiology* 14:396-402 (1995).

Verwoerd et al., "Stable Accumulation of *Aspergillus niger* Phytase in Transgenic Tobacco Leaves," *Plant Physiol.* 109:1199-1205 (1995).

Brøndsted et al., "Effect of Growth Conditions on Expression of the Acid Phosphatase (*cyx-appA*) Operon and the *appY* Gene, Which Encodes a Transcriptional Activator of *Escherichia coli*," *Journal of Bacteriology* 178(6):1556-1564 (1996).

Divakaran et al., "In Vitro Studies on the Interaction of Phytase with Trypsin and Amylase Extracted from Shrimp (*Penaeus vannamei*) Hepatopancreas," *J. Agric. Food Chem.* 46:4973-4976 (1998).

Jia et al., "Purification, Crystallization and Preliminary X-ray Analysis of the *Escherichia coli* Phytase," *Acta Cryst,* D54:647-649 (1998).

Kerovuo et al., "Isolation, Characterization, Molecular Gene Cloning, and Sequencing of a Novel Phytase from *Bacillus subtilis*," *Applied and Environmental Microbiology* 64(6):2079-2085 (1998).

Kim et al., "Cloning of the Thermostable Phytase Gene (*phy* ) from *Bacillus* sp. DS11 and its Overexpression in *Escherichia coli*," *FEMS Microbiology Letters* 162:185-191 (1998).

Han et al., "Role of Glycosylation in the Functional Expression of an *Aspergillus niger* Phytase (*phyA*) in *Pichia pastoris*," *Archives of Biochemistry and Biophysics* 364(1):83-90 (1999).

Wyss et al., "Biophysical Characterization of Fungal Phytases (*myo*-Inositol Hexakisphosphate Phosphohydrolases): Molecular Size, Glycosylation Pattern, and Engineering of Proteolytic Resistance," *Applied and Environmental Microbiology* 65(2):359-366 (1999).

Wyss et al., "Biochemical Characterization of Fungal Phytases (*myo*-Inositol Hexakisphosphate Phosphohydrolases): Catalytic Properties," *Applied and Enviromental Microbiology* 65(2):367-373 (1999).

Rodriguez et al., "Different Sensitivity of Recombinant *Aspergillus niger* Phytase (r-PhyA) and *Escherichia coli* pH 2.5 Acid Phosphatase (r-AppA) to Trypsin and Pepsin in Vitro," *Archives of Biochemistry and Biophysics* 365(2):262-267 (1999).

Rodriguez et al., "Cloning, Sequencing, and Expression of an *Escherichia coli* Acid Phosphatase/Phytase Gene (*appA2*) Isolated from Pig Colon," *Biochemical and Biophysical Research Communications* 257:117-123 (1999).

Murray et al., "Construction of Artificial Chromosomes in Yeast," *Nature* 305:189-193 (1983).

Greiner et al., "Purification and Characterization of Two Phytases from *Escherichia coli*," *Archives of Biochemistry and Biophysics* 303:107-113 (1993).

Minamiguchi et al., "Secretive Expression of the *Aspergillus aculeatus* Cellulase (FI-CM Case) by *Saccharomyces cerevisiae*," *Journal of Fermentation and Bioengineering* 79(4):363-366 (1995).

Wodzinski et al., "Phytase," *Advances in Applied Microbiology* 42:263-302 (1996).

Konietzny et al., "Model Systems for Developing Detection Methods for Foods Deriving from Genetic Engineering," *Journal of Food Composition and Analysis* 10:28-35 (1997).

Sun et al., "Expression of *Aspergillus niger* Phytase in Yeast *Saccharomyces cerevisiae* for Poultry Diet Supplementation," 76:5 (1997) (abstract only).

Yao et al., "Recombinant *Pichia pastoris* Overexpressing Bioactive Phytase," *Science in China (Series C) Life Sciences* 41(3):330-336 (1998).

Han et al., "Expression of an *Aspergillus niger* Phytase Gene (*phyA*) in *Saccharomyces cerevisiae*," *Applied and Enviromental Microbiology* 65(5):1915-1918 (1999).

Maugenest et al., "Cloning and Characterization of cDNA Encoding a Maize Seedling Phytase," *Biochem. J.* 322:511-517 (1997).

Tschopp et al., "Heterologous Gene Expression in Methylotrophic Yeast," *Biotechnology*, 18:305-322 (1991).

Kumagai et al., "Conversion of Starch to Ethanol in a Recombinant *Saccharomyces cerevisiae* Strain Expression Ric α-amylase from a Novel *Pichia pastoris* Alcohol Oxidase Promoter," *Biotechnology* 11:606-610 (1993).

van Hartingsveldt et al., "Cloning, Characterization and Overexpression of the Phytase-Encoding Gene (*phyA*) of *Aspergillus niger*," *Gene* 127:87-94 (1993).

Phillippy et al., "Expression of an *Aspergillus niger* Phytase (*phyA*) in *Escherichia coli*," *J. Agric. Food Chem.* 45(8):3337-3342 (1997).

Rodriguez et al., "Site-Directed Mutagenesis Improves Catalytic Efficiency and Thermostability of *Escherichia coli* pH 2.5 Acid Phosphatase/Phytase Expressed in *Pichia pastoris*," *Archives of Biochemistry and Biophysics* 382(1):105-112 (2000).

Boer et al., "Characterization of *Trichoderma reesei* Cellobiohydrolase Cel7a Secreted from *Pichia pastoris* Using Two Different Promoters," *Biotechnology and Bioengineering* 69(5):486-494 (2000).

Takahashi et al., "Independent Production of Two Molecular Forms of a Recombinant *Rhizopus oryzae* Lipase by *KEX2*-Engineered Strains of *Saccharomyces cerevisiae*," *Applied Microbiol. Biotechnology*, 52(4):534-540 (1999).

Meldgaard et al., "Different Effects of *N*-Glycosylation on the Thermostability of Highly Homologous Bacterial (1,3-1,4)-β-Glucanases Secreted from Yeast," *Microbiology* 140(1):159-166 (1994).

Kanai et al., "Recombinant Thermostable Cycloinulo-oligosaccharide Fructanotransferase Produced by *Saccharomyces cerevisiae*," *Appl. Environ. Microbiol.* 63(12):4956-4960 (1997).

Terashima et al., "The Roles of the N-Linked Carbohydrate Chain of Rice α-amylase in Thermostability and Enzyme Kinetics," *Eur. J. Biochem.* 226:249-254 (1994).

Atlung et al., "Role of the Transcriptional Activator AppY in Regulation of the *cyx appA* Operon of *Escherichia coli* by Anaerobiosis, Phosphate Starvation, and Growth Phase," *Journal of Bacteriology* 176(17):5414-5422 (1994).

Belin et al., "A Pleî otropic Acid Phosphatase-Deficient Mutant of *Excherichia coli* Shows Premature Termination in the *dsbA* Gene. Use of *dsbA::phoaA* Fusions to Localize a Structurally Important Domain in DsbA," *Mol. Gen. Genet.* 242:23-32 (1994).

Chiarugi et al., "Differential Role of Four Cysteines on the Activity of a Low $M_r$ Phosphotyrosine Protein Phosphatase," *FEBS LETTERS* 310(1):9-12 (1992).

Lim et al., "Crystal Structure of *Escherichia coli* Phytase and its Complex with Phytate," *Nature Structural Biology* 7(2): 108-113 (2000).

Atcc Catalog for Yeasts, 19th Edition (1995), pp. 20-22.

Boctor et al., "Enhancement of the Stability of Thrombin by Polyols: Microcalorimetric Studies, " *J. Pharm. Pharmacol.*, 44:600-603 (1992).

Gen Bank Accession No. B36733, Apr. 23, 1993, corresponding to Greiner et al., Arch. Biochem. Biophys., 303:107-113 (1993).

DSM Nutritional Products, Opposition Brief for European Patent No. Ep 1-090-129 (10 pages) (Nov. 15, 2006).

Genebank Accession No. AAB96872 (Jan. 16, 1998).

Genebank Accession No. M94550 (Apr. 27, 1993).

Golovan et al., "Characterization and Overproduction of the E. coli appA Encoded Biofunctional Enzyme the Exhibits Both Phytase and Acid Phosphatase Activities, " *Can. J. Microbiol.* 46:59-71 (2000).

Greiner et al., "Purification and Characterization of a Phytase from *Klebsiella terrigena*, " *Archives of Biochecmistry and Biophysics* 341(2):201-206 (1997).

Han et al., "Development of Phytase Overexpressing Microbes for Nutritional Use, " Poster Presentation at Cornell University's Biotechnology Symposium, Ithaca, New York (Oct. 15, 1997).

Kostrewa et al., "Crystal Structure of *Aspergillus niger* ph 2.5 Acid Phosphatase at 2.4 A Resoloution, " *J. Mol. Biol.* 288:965-974 (1999).

Kostrewa et al., "Crystal Structure of Phytase from *Aspergillus ficuum* at 2.5 A Resolution, " *Nat. Struct. Biol.* 4:185-190 (1997).

Lehmann et al., "Exchanging the Active Site Between Phytases for Altering the Functional Properties of the Enzyme, " *Protein Sci.* 9(10):1866-1872 (2000).

Lehmann et al., "From DNA Sequence to Improved Functionality: Using Protein Sequence Comparisons to Rapidly Design a Thermostable Consensus Phytase, " *Protein Eng.* 13(1):49-57 (2000).

Lei et al., "Biotechnological Developments of Effective Phytases for Mineral Nutrition and Environmental Protection, " *Appl. Microb. Biotech.* 57(4):474-481 (2001).

Lei et al., "Calcium Level Affects the Efficacy of Supplemental Microbial Phytase in Corn-Soybean Meal Diets of Weanling Pigs, " *J. Anim. Sci.* 72(1):139-143 (1994).

Lei et al., "Nutritional Benefits of Phytase and Dietary Determinants of its Efficacy, " *J. Appl. Anim. Res.* 17:97-112 (2000).

Lei et al., "Supplemental Microbial Phytase Improves Bioavailability of Dietary Zinc to Weanling Pigs, " *J. Nutr.* 123:1117-1123 (1993).

Lei et al., "Supplementing Corn-Soybean Meal Diets with Microbial Phytase Linearly Improves Phytate Phosphorus Utilization by Weanling Pigs, " *J. Anim. Sci.* 71:3359-3367 (1993).

Lim et al., "Studies of Reaction Kinetics in Relation to the $T_g$ of Polymers in Frozen Model Systems, " in Levine, eds., *Water Relationships in Food*, New York, NY:Plenum Press, pp. 103-122 (1991).

Lozano et al., "Effect of Polyols on a-Chymotrypsin Thermostability: A Mechanistic Analysis of the Enzyme Stabilization, " *J. Biotechnol.*, 35:9-18 (1994).

Lozano et al., "Influence of Polyhydroxylic Cosolvents on Papain Thermostability," *Enzyme Microb. Technol.*, 15:868-873 (1993).

Mitchell et al., "The Phytase Subfamily of Histidine Acid Phosphatases: Isolation of Genes for Two Novel Phytases from the Fungi *Aspergillus terreus* and *Myceliophthora thermophila*," *Microbiology* 143:245-252 (1997).

Mullaney et al., "Advances in Phytase Research," *Advances in Applied Microbiology* 47:157-199 (2000).

Mullaney et al., "Phytase Activity in *Aspergillus fumigatus* Isolates," *Biochem. Biophys. Res. Commun.* 275:759-763 (2000).

Mullaney et al., "Positive Identification of a Lambda gt11 Clone Containing a Region of Fungal Phytase Gene by Immunoprobe and Sequence Verification," *Appl. Microbiol. Biotechnol.* 35:611-614 (1991).

Nielsen et al., "The Determinants of α-Amylase pH-Activity Profiles," *Protein Eng.* 14(8):505-512 (2001).

Novozymes A/S, Opposition Brief for European Patent No. EP 1-090-129 (19 pages) (Nov. 2006).

Pasamontes et al., "Gene Cloning, Purification, and Characterization of a Heat-Stable Phytase from the Fungus *Aspergillus fumigatus*," *Appl. Environ. Microbiol.* 63(5):1696-1700 (1997).

Rodriguez et al., "Expression of the *Aspergillus fumigatus* Phytase Gene in *Pichia pastoris* and Characterization of the Recombinant Enzyme," *Biochem. Biophys. Res. Commun.* 268:373-378 (2000).

Rossi et al., "Stabilization of the Restriction Enzyme *Eco*RI Dried with Trehalose and Other Selected Glass-Forming Solutes," *Biotechnol. Prog.*, 13:609-616 (1997).

Schebor et al., "Glassy State and Thermal Inactivation of Invertase and Lactase in Dried Amorphous Matrices," *Biotechnol. Prog.*, 13:857-863 (1997).

Tomschy et al., "Active Site Residue 297 of *Aspergillus niger* Phytase Critically Affects the Catalytic Properties," *FEBS Lett.* 472(2-3):169-172 (2000).

Tomschy et al., "Optimization of the Catalytic Properties of *Aspergillus fumigatus* Phytase Based on the Three-Dimensional Structure," *Protein Sci.* 9(7):1304-1311 (2000).

Ullah, A.H.J., "Aspergillus Ficuum Phytase: Partial Primary Structure, Substrate Selectivity, and Kinetic Characterization," *Preparative Biochemistry* 18(4):459-471 (1988).

Ullah et al., "Cyclohexanedione Modification of Arginine at the Active Site of *Aspergillus ficuum* Phytase," *Biochem. Biophys. Res. Commun.* 178(1):45-53 (1991).

Ullah et al., "Extracellular Phytase (E.C. 3.1.3.8) from *Aspergillus ficuum* NRRL 3135: Purification and Characterization," *Prep. Biochem.* 17(1):63-91 (1987).

Van Dijck, P.W.M., "Chymosin and Phytase. Made by Genetic Engineering (No. 10 in a Series of Articles to Promote a Better Understanding of the Use of Genetic Engineering)," *J. Biotechnology* 67:77-80 (1999).

Van Etten et al., "Covalent Structure, Disulfide Bonding, and Identification of Reactive Surface and Active Site Residues of Human Prostatic Acid Phosphatase," *J. Biol. Chem.* 266(4):2313-2319 (1991).

Yi et al., "Sites of Phytase Activity in the Gastrointestinal Tract of Young Pigs," *Animal Feed Science Technology* 61:361-368 (1996).

Leeson et al., "Efficacy of New Bacterial Phytase in Poultry Diets," *Can. J. Anim. Sci.* 80:527-528 (2000).

Murray et al., "The Effect of Microbial Phytase in a Pearl Millet-Soybean Meal Diet on Apparent Digestibility and Retention of Nutrients, Serum Mineral Concentration, and Bone Mineral Density of Nursery Pigs," *J. Animal Sci.* 75:1284-1291 (1997).

Scott et al., "The Effect of Phosphorus, Phytase Enzyme, and Calcium on the Performance of Layers Fed Corn-Based Diets," *Poultry Sci.* 78:1742-1749 (1999).

Sebastian et al., "Apparent Digestibility of Protein and Amino Acids in Brioler Chickens Fed a Corn-Soybean Diet Supplemented with Microbial Phytase," *Poultry Sci.* 76:1760-1769 (1997).

Ullah et al., "Differences in the Active Site Environment of *Aspergillus ficuum* Phytases," *Biochem. Biophys. Res. Comm.* 243:458-462 (1998).

```
  1 taaggagcagaaaca ATG TGG TAT TTA CTT TGG TTC GTC GGC ATT TTG TTG ATG TGT TCG CTC   63
  1                  M   W   Y   L   L   W   F   V   G   I   L   L   M   C   S   L    16

64 TCC ACC CTT GTG TTG GTA TGG CTG GAC CCG CGA TTG AAA AGT Taacgaacgtaggcctgatgcggcg 128
 17  S   T   L   V   L   V   W   L   D   P   R   L   K   S   *                        31

129 cattagcatcgcatcaggcaatcaataatgtcagatatgaaaagcggaaacatatcgATG AAA GCG ATC TTA ATC  201
  1                                                           M   K   A   I   L   I    6
                                                                         E2 ─────────
202 CCA TTT TTA TCT CTT CTG ATT CCG TTA ACC CCG CAA TCT GCA TTC GCT CAG AGT GAG CCG   261
  7  P   F   L   S   L   L   I   P   L   T   P   Q   S   A   F   A   Q   S   E   P    26
     →
262 GAG CTG AAG CTG GAA AGT GTG GTG ATT GTC AGC CGT CAT GGT GTG CGT GCC CCA ACC AAG   321
 27  E   L   K   L   E   S   V   V   I   V   S   R   H   G   V   R   A   P   T   K    46

322 GCC ACG CAA CTG ATG CAG GAT GTC ACC CCA GAC GCA TGG CCA ACC TGG CCG GTA AAA CTG   381
 47  A   T   Q   L   M   Q   D   V   T   P   D   A   W   P   T   W   P   V   K   L    66

382 GGT TGG CTG ACA CCA CGC GGT GGT GAG CTA ATC GCC TAT CTC GGA CAT TAC CAA CGC CAG   441
 67  G   W   L   T   P   R   G   G   E   L   I   A   Y   L   G   H   Y   Q   R   Q    86

442 CGT CTG GTG GCC GAC GGA TTG CTG GCG AAA AAG GGC TGC CCG CAG CCT GGT CAG GTC GCG   501
 87  R   L   V   A   D   G   L   L   A   K   K   G   C   P   Q   P   G   Q   V   A   106

502 ATT ATT GCT GAT GTC GAC GAG CGT ACC AAA ACA GGC GAA GCC TTC GCC GCC GGG CTG       561
107  I   I   A   D   V   D   E   R   T   R   K   T   G   E   A   F   A   A   G   L   126
                                                A1
562 GCA CCT GAC TGT GCA ATA ACC GTA CAT ACC CAG GCA GAT ACG TCC AGT CCC GAT CCG TTA   621
127  A   P   D   C   A   I   T   V   H   T   Q   A   D   T   S   S   P   D   P   L   146

622 TTT AAT CCT CTA AAA ACT GGC GTT TGC CAA CTG GAT AAC GCG AAC GTG ACT GAC GCG ATC   681
147  F   N   P   L   K   T   G   V   C   Q   L   D   N   A   N   V   T   D   A   I   166

682 CTC AGC AGG GCA GGA GGG TCA ATT GCT GAC TTT ACC GGG CAT CGG CAA ACG GCG TTT CGC   741
167  L   S   R   A   G   G   S   I   A   D   F   T   G   H   R   Q   T   A   F   R   186
                                             P2 ───────────────────────►◄──
742 GAA CTG GAA CGG GTG CTT AAT TTT CCG CAA TCA AAC TTG TGC CTT AAA CGT GAG AAA CAG   801
187  E   L   E   R   V   L   N   F   P   Q   S   N   L   C   L   K   R   E   K   Q   206
                                             P3
802 GAC GAA AGC TGT TCA TTA ACG CAG GCA TTA CCA TCG GAA CTC AAG GTG AGC GCC GAC AAT   861
207  D   E   S   C   S   L   T   Q   A   L   P   S   E   L   K   V   S   A   D   N   226

862 GTT TCA TTA ACC GGT GCG GTA AGC CTC GCA TCA ATG CTG ACG GAA ATA TTT CTC CTG CAA   921
227  V   S   L   T   G   A   V   S   L   A   S   M   L   T   E   I   F   L   L   Q   246

922 CAA GCA CAG GGA ATG CCG GAG CCG GGG TGG GGA AGG ATC ACT GAT TCA CAC CAG TGG AAC   981
247  Q   A   Q   G   M   P   E   P   G   W   G   R   I   T   D   S   H   Q   W   N   266

982 ACC TTG CTA AGT TTG CAT AAC GCG CAA TTT TAT TTA CTA CAA CGC ACG CCA GAG GTT GCC  1041
267  T   L   L   S   L   H   N   A   Q   F   Y   L   L   Q   R   T   P   E   V   A   286

1042 CGC AGT CGC GCC ACC CCG TTA TTG GAT TTG ATC AAG ACA GCG TTG ACG CCC CAT CCA CCG 1101
287   R   S   R   A   T   P   L   L   D   L   I   K   T   A   L   T   P   H   P   P  306

1102 CAA AAA CAG GCG TAT GGT GTG ACA TTA CCC ACT TCA GTG CTG TTT ATT GCC GGA CAC GAT 1161
307   Q   K   Q   A   Y   G   V   T   L   P   T   S   V   L   F   I   A   G   H   D  326

1162 ACT AAT CTG GCA AAT CTC GGC GGC GCA CTG GAG CTC AAC TGG ACG CTT CCA GGT CAG CCG 1221
327   T   N   L   A   N   L   G   G   A   L   E   L   N   W   T   L   P   G   Q   P  346

1222 GAT AAC ACG CCG CCA GGT GGT GAA CTG GTG TTT GAA CGC TGG CGT CGG CTA AGC GAT AAC 1281
347   D   N   T   P   P   G   G   E   L   V   F   E   R   W   R   R   L   S   D   N  366

1282 AGC CAG TGG ATT CAG GTT TCG CTG GTC TTC CAG ACT TTA CAG CAG ATG CGT GAT AAA ACG 1341
367   S   Q   W   I   Q   V   S   L   V   F   Q   T   L   Q   Q   M   R   D   K   T  386

1342 CCG CTA TCA TTA AAT ACG CCG CCC GGA GAG GTG AAA CTG ACC CTG GCA GGA TGT GAA GAG 1401
387   P   L   S   L   N   T   P   P   G   E   V   K   L   T   L   A   G   C   E   E  406

1402 CGA AAT GCG CAG GGC ATG TGT TCG TTG GCC GGT TTT ACG CAA ATC GTG AAT GAA GCG CGC 1461
407   R   N   A   Q   G   M   C   S   L   A   G   F   T   Q   I   V   N   E   A   R  426
                                   ─── K2
1462 ATA CCG GCG TGC AGT TTG TAA                                                     1491
427   I   P   A   C   S   L   *                                                        433
```

FIGURE 1

SEQUENCE LISTING

<160> NUMBER OF SEQ ID NOS: 9

<210> SEQ ID NO 1
<211> LENGTH: 432
<212> TYPE: PRT
<213> ORGANISM: Escherichia coli

<400> SEQUENCE: 1

```
Met Lys Ala Ile Leu Ile Pro Phe Leu Ser Leu Leu Ile Pro Leu Thr
 1               5                  10                  15

Pro Gln Ser Ala Phe Ala Gln Ser Glu Pro Glu Leu Lys Leu Glu Ser
             20                  25                  30

Val Val Ile Val Ser Arg His Gly Val Arg Ala Pro Thr Lys Ala Thr
         35                  40                  45

Gln Leu Met Gln Asp Val Thr Pro Asp Ala Trp Pro Thr Trp Pro Val
     50                  55                  60

Lys Leu Gly Trp Leu Thr Pro Arg Gly Gly Glu Leu Ile Ala Tyr Leu
 65                  70                  75                  80

Gly His Tyr Gln Arg Gln Arg Leu Val Ala Asp Gly Leu Leu Ala Lys
                 85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
```

```
                130                 135                 140
Pro Leu Phe Asn Pro Leu Lys Thr Gly Val Cys Gln Leu Asp Asn Ala
145                 150                 155                 160
Asn Val Thr Asp Ala Ile Leu Ser Arg Ala Gly Gly Ser Ile Ala Asp
                165                 170                 175
Phe Thr Gly His Arg Gln Thr Ala Phe Arg Glu Leu Glu Arg Val Leu
                180                 185                 190
Asn Phe Pro Gln Ser Asn Leu Cys Leu Lys Arg Glu Lys Gln Asp Glu
                195                 200                 205
Ser Cys Ser Leu Thr Gln Ala Leu Pro Ser Glu Leu Lys Val Ser Ala
    210                 215                 220
Asp Asn Val Ser Leu Thr Gly Ala Val Ser Leu Ala Ser Met Leu Thr
225                 230                 235                 240
Glu Ile Phe Leu Leu Gln Gln Ala Gln Gly Met Pro Glu Pro Gly Trp
                245                 250                 255
Gly Arg Ile Thr Asp Ser His Gln Trp Asn Thr Leu Leu Ser Leu His
                260                 265                 270
Asn Ala Gln Phe Tyr Leu Leu Gln Arg Thr Pro Glu Val Ala Arg Ser
                275                 280                 285
Arg Ala Thr Pro Leu Leu Asp Leu Ile Lys Thr Ala Leu Thr Pro His
                290                 295                 300
Pro Pro Gln Lys Gln Ala Tyr Gly Val Thr Leu Pro Thr Ser Val Leu
305                 310                 315                 320
Phe Ile Ala Gly His Asp Thr Asn Leu Ala Asn Leu Gly Gly Ala Leu
                325                 330                 335
Glu Leu Asn Trp Thr Leu Pro Gly Gln Pro Asp Asn Thr Pro Pro Gly
                340                 345                 350
Gly Glu Leu Val Phe Glu Arg Trp Arg Arg Leu Ser Asp Asn Ser Gln
                355                 360                 365
Trp Ile Gln Val Ser Leu Val Phe Gln Thr Leu Gln Gln Met Arg Asp
                370                 375                 380
Lys Thr Pro Leu Ser Leu Asn Thr Pro Pro Gly Glu Val Lys Leu Thr
385                 390                 395                 400
Leu Ala Gly Cys Glu Glu Arg Asn Ala Gln Gly Met Cys Ser Leu Ala
                405                 410                 415
Gly Phe Thr Gln Ile Val Asn Glu Ala Arg Ile Pro Ala Cys Ser Leu
                420                 425                 430

<210> SEQ ID NO 2
<211> LENGTH: 1486
<212> TYPE: DNA
<213> ORGANISM: Escherichia coli

<400> SEQUENCE: 2
taaggagcag aaacaatgtg gtatttactt tggttcgtcg gcattttgtt gatgtgttcg    60
ctctccaccc ttgtgttggt atggctggac ccgcgattga aaagttaacg aacgtaggcc   120
tgatgcggcg cattagcatc gcatcaggca atcaataatg tcagatatga aaagcggaaa   180
catatcgatg aaagcgatct taatcccatt tttatctctt ctgattccgt taaccccgca   240
atctgcattc gctcagagtg agccggagct gaagctggaa agtgtggtga ttgtcagccg   300
tcatggtgtg cgtgccccaa ccaaggccac gcaactgatg caggatgtca ccccagacgc   360
atggccaacc tggccggtaa aactgggttg gctgacacca cgcggtggtg agctaatcgc   420
ctatctcgga cattaccaac gccagcgtct ggtggccgac ggattgctgg cgaaaaaggg   480
```

```
ctgcccgcag cctggtcagg tcgcgattat tgtcgatgtc gacgagcgta cccgtaaaac    540
aggcgaagcc ttcgccgccg ggctggcacc tgactgtgca ataaccgtac atacccaggc    600
agatacgtcc agtcccgatc cgttatttat tcctctaaaa actggcgttt gccaactgga    660
taacgcgaac gtgactgacg cgatcctcag cagggcagga gggtcaattg ctgactttac    720
cgggcatcgg caaacggcgt tcgcgaact ggaacgggtg cttaattttc cgcaatcaaa     780
cttgtgcctt aaacgtgaga acaggacga aagctgttca ttaacgcagg cattaccatc     840
ggaactcaag gtgagcgccg acaatgtttc attaaccggt gcggtaagcc tcgcatcaat    900
gctgacggaa atatttctcc tgcaacaagc acagggaatg ccggagccgg ggtggggaag    960
gatcactgat tcacaccagt ggaacaccTt gctaagtttg cataacgcgc aattttattt   1020
actacaacgc acgccagagg ttgcccgcag tcgcgccacc ccgttattgg atttgatcaa   1080
gacagcgttg acgccccatc caccgcaaaa acaggcgtat ggtgtgacat tacccacttc   1140
agtgctgttt attgccggac acgatactaa tctgcaaat ctcggcggcg cactggagct    1200
caactggacg cttccaggtc agccggataa cacgccgcca ggtggtgaac tggtgtttga   1260
acgctggcgt cggctaagcg ataacagcca gtggattcag gtttcgctgg tcttccagac   1320
tttacagcag atgcgtgata aaacgccgct atcattaaat acgccgcccg gagaggtgaa   1380
actgaccctg gcaggatgtg aagagcgaaa tgcgcagggc atgtgttcgt tggccggttt   1440
tacgcaaatc gtgaatgaag cgcgcatacc ggcgtgcagt ttgtaa                  1486
```

<210> SEQ ID NO 3
<211> LENGTH: 432
<212> TYPE: PRT
<213> ORGANISM: Escherichia coli

<400> SEQUENCE: 3

```
Met Lys Ala Ile Leu Ile Pro Phe Leu Ser Leu Leu Ile Pro Leu Thr
  1               5                  10                  15

Pro Gln Ser Ala Phe Ala Gln Ser Glu Pro Glu Leu Lys Leu Glu Ser
             20                  25                  30

Val Val Ile Val Ser Arg His Gly Val Arg Ala Pro Thr Lys Ala Thr
         35                  40                  45

Gln Leu Met Gln Asp Val Thr Pro Asp Ala Trp Pro Thr Trp Pro Val
     50                  55                  60

Lys Leu Gly Trp Leu Thr Pro Arg Gly Gly Glu Leu Ile Ala Tyr Leu
 65                  70                  75                  80

Gly His Tyr Gln Arg Gln Arg Leu Val Ala Asp Gly Leu Leu Ala Lys
                 85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190
```

-continued

```
Asn Phe Pro Gln Ser Asn Leu Asn Leu Lys Arg Glu Lys Gln Asn Glu
            195                 200                 205

Ser Cys Asn Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
    370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430
```

<210> SEQ ID NO 4
<211> LENGTH: 1486
<212> TYPE: DNA
<213> ORGANISM: Escherichia coli

<400> SEQUENCE: 4

```
taaggagcag aaacaatgtg gtatttactt tggttcgtcg gcattttgtt gatgtgttcg      60
ctctccaccc ttgtgttggt atggctggac ccgcgattga aagttaacg aacgtaggcc     120 tgatgcggcg cattagcatc gcatcaggca atcaataatg tcagatatga aaagcggaaa     180
catatcgatg aaagcgatct taatcccatt tttatctctt ctgattccgt taaccccgca     240
atctgcattc gctcagagtg agccggagct gaagctggaa agtgtggtga ttgtcagccg     300
tcatggtgtg cgtgccccaa ccaaggccac gcaactgatg caggatgtca ccccagacgc     360
atggccaacc tggccggtaa aactgggttg gctgacacca cgcggtggtg agctaatcgc     420
ctatctcgga cattaccaac gccagcgtct ggtggccgac ggattgctgg cgaaaaaggg     480
ctgcccgcag cctggtcagg tcgcgattat tgtcgatgtc gacgagcgta cccgtaaaac     540
aggcgaagcc ttcgccgccg ggctggcacc tgactgtgca ataaccgtac atacccaggc     600
agatacgtcc agtcccgatc cgttatttat tcctctaaaa actggcgttt gccaactgga     660
taacgcgaac gtgactgacg cgatcctcag cagggcagga gggtcaattg ctgacttac     720 cgggcatcgg caaacggcgt ttcgcgaact ggaacgggtg cttaatttc cgcaatcaaa     780
```

```
cttgaacctt aaacgtgaga aacagaatga aagctgtaac ttaacgcagg cattaccatc    840
ggaactcaag gtgagcgccg acaatgtttc attaaccggt gcggtaagcc tcgcatcaat    900
gctgacggaa atatttctcc tgcaacaagc acagggaatg ccggagccgg ggtggggaag    960
gatcactgat tcacaccagt ggaacacctt gctaagtttg cataacgcgc aattttattt   1020
actacaacgc acgccagagg ttgcccgcag tcgcgccacc ccgttattgg atttgatcaa   1080
gacagcgttg acgcccatc caccgcaaaa acaggcgtat ggtgtgacat tacccacttc   1140
agtgctgttt attgccggac acgatactaa tctgcaaaat ctcggcggcg cactggagct   1200
caactggacg cttccaggtc agccggataa cacgccgcca ggtggtgaac tggtgtttga   1260
acgctggcgt cggctaagcg ataacagcca gtggattcag gtttcgctgg tcttccagac   1320
tttacagcag atgcgtgata aaacgccgct atcattaaat acgccgcccg gagaggtgaa   1380
actgaccctg gcaggatgtg aagagcgaaa tgcgcagggc atgtgttcgt tggccggttt   1440
tacgcaaatc gtgaatgaag cgcgcatacc ggcgtgcagt ttgtaa                  1486
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
ggaattcgct cagagccgga                                                 20

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ctgggtatgg ttggttatat tacagtcagg t                                    31

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
caaacttgaa ccttaaacgt gag                                             23

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
cctgcgttaa gttacagctt tcattctgtt t                                    31

<210> SEQ ID NO 9
<211> LENGTH: 22

```
-continued
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9 ggggtaccttt acaaactgca cg                                              22
```

SITE-DIRECTED MUTAGENESIS OF ESCHERICHIA COLI PHYTASE

The present application is a divisional of U.S. patent application Ser. No. 09/715,477, filed Nov. 17, 2000, now U.S. Pat No. 6,841,370 which claims the benefit of U.S. Provisional Patent Application Ser. No. 60/166,179, filed Nov. 18, 1999, which are hereby incorporated by reference in their entirety.

FIELD OF THE INVENTION

The present invention is directed to the site-directed mutagenesis of *Escherichia coli* phosphatase/phytase.

BACKGROUND OF THE INVENTION

Phytases, a specific group of monoester phosphatases, are required to initiate the release of phosphate ("P") from phytate (myo-inositol hexophosphate), the major storage form of P in cereal foods or feeds (Reddy, N. R. et al., "Phytates in Legumes and Cereals," *Advances in Food Research*, 28:1 (1982)). Because simple-stomached animals like swine and poultry as well as humans have little phytase activity in their gastrointestinal tracts, nearly all of the ingested phytate P is indigestible. This results in the need for supplementation of inorganic P, an expensive and non-renewable nutrient, in diets for these animals. More undesirably, the unutilized phytate-P excreted through manure of these animals becomes P pollution of the environment (Cromwell, G. L. et al., "P- A Key Essential Nutrient, Yet a Possible Major Pollutant—Its Central Role in Animal Nutrition," *Biotechnology In the Feed Industry*; Proceedings Alltech 7th Annual Symposium, p. 133 (1991)). Furthermore, phytate chelates with essential trace elements like zinc and produces nutrient deficiencies such as growth and mental retardation in children ingesting mainly plant origin foods without removal of phytate.

Two phytases, phyA and phyB, from *Aspergillus niger* NRRL3135 have been cloned and sequenced (Ehrlich, K. C. et al., "Identification and Cloning of a Second Phytase Gene (phys) from *Aspergillus niger* (ficuum)," *Biochem. Biophys. Res. Commun.*, 195:53–57 (1993); Piddington, C. S. et al., "The Cloning and Sequencing of the Genes Encoding Phytase (phy) and pH 2.5-optimum Acid Phosphatase (aph) from *Aspergillus niger* var. *awamori*," *Gene* 133:56–62 (1993)). Recently, new phytase genes have been isolated from *Aspergillus terreus* and *Myceliophthora thermophila* (Mitchell et al., "The Phytase Subfamily of Histidine Acid Phosphatases: Isolation of Genes for Two Novel Phytases From the Fungi *Aspergillus terreus* and *Myceliophthora thermophila*," *Microbiology* 143:245–52, (1997)), *Aspergillus fumigatus* (Pasamontes et al., "Gene Cloning, Purification, and Characterization of a Heat-Stable Phytase from the Fungus *Aspergillus fumigatus*" *Appl. Environ. Microbiol.*, 63:1696–700 (1997)), *Emericella nidulans* and *Talaromyces thermophilus* (Pasamontes et al., "Cloning of the Phytase from *Emericella nidulans* and the Thermophilic Fungus *Talaromyces thernophilus*," *Biochim. Biophys. Acta.* 1353: 217–23 (1997)), and maize (Maugenest et al., "Cloning and Characterization of a cDNA Encoding a Maize Seedling Phytase," *Biochem. J.* 322:511–17 (1997)).

Various types of phytase enzymes have been isolated and/or purified from *Enterobacter* sp. 4 (Yoon et al., "Isolation and Identification of Phytase-Producing Bacterium, *Enterobacter* sp. 4, and Enzymatic Properties of Phytase Enzyme.," *Enzyme and Microbial Technology* 18:449–54 (1996)), *Klebsiella terrigena* (Greiner et al., "Purification and Characterization of a Phytase from *Klebsiella terrigena*," *Arch. Biochem. Biophys.* 341:201–06 (1997)), and *Bacillus* sp. DS11 (Kim et al., "Purification and Properties of a Thermostable Phytase from *Bacillus* sp. DS11," *Enzyme and Microbial Technology* 22:2–7 (1998)). Properties of these enzyme have been studied. In addition, the crystal structure of phyA from *Aspergillus ficuum* has been reported (Kostrewa et al., "Crystal Structure of Phytase from *Aspergillus ficuum* at 2.5 A Resolution," *Nature Structure Biology* 4:185–90 (1997)).

Hartingsveldt et al. introduced phyA gene into *A. niger* and obtained a ten-fold increase of phytase activity compared to the wild type. ("Cloning, Characterization and Overexpression of the Phytase-Encoding Gene (phyA) of *Aspergillus Niger*," *Gene* 127:87–94 (1993)). Supplemental microbial phytase of this source in the diets for pigs and poultry has been shown to be effective in improving utilization of phytate-P and zinc (Simons et al., "Improvement of Phosphorus Availability By Microbial Phytase in Broilers and Pigs," *Br. J. Nutr.* 64:525 (1990); Lei, X. G. et al., "Supplementing Corn-Soybean Meal Diets With Microbial Phytase Linearly Improves Phytate P Utilization by Weaning Pigs," *J. Anim. Sci.*, 71:3359 (1993); Lei, X. G. et al., "Supplementing Corn-Soybean Meal Diets With Microbial Phytase Maximizes Phytate P Utilization by Weaning Pigs," *J. Anim. Sci.* 71:3368 (1993); Cromwell, G. L. et al., "P- A Key Essential Nutrient, Yet a Possible Major Pollutant—Its Central Role in Animal Nutrition," *Biotechnology In the Feed Industry*; Proceedings Alltech 7th Annual Symposium, p. 133 (1991)). However, the cost of the limited commercial phytase supply and its instability when subjected to heat during feed pelleting preclude its practical use in animal industry (Jongbloed, A. W. et al., "Effect of Pelleting Mixed Feeds on Phytase Activity and Apparent Absorbability of Phosphorus and Calcium in Pigs," *Animal Feed Science and Technology*, 28:233–42 (1990)). Moreover, phytase produced from *A. niger* is presumably not the safest source for human food manufacturing.

Thus, there is a need to improve phytase production for application by the food and feed industry.

SUMMARY OF THE INVENTION

The present invention relates to an isolated mutant acid phosphatase/phytase which is produced by making a plurality of amino acid substitutions in a wild-type *Escherichia coli* acid phosphatase/phytase having an amino acid sequence of SEQ. ID. No. 1. These amino acid substitutions are made at positions 200, 207, and 211 of SEQ. ID. No. 1. The present invention also involves an isolated mutant acid phosphatase/phytase which differs from the wild-type acid phosphatase/phytase having an amino acid sequence of SEQ. ID. No 1 by at least one amino acid substitution which disrupts disulfide bond formation between Cys amino acid residues at positions 200 and 210. The mutant acid phosphatase/phytase of the present invention is useful in animal feed compositions.

The present invention also relates to a method for improving the enzymatic properties of a wild-type *Escherichia coli* acid phosphatase/phytase having an amino acid sequence of SEQ. ID. No. 1. This method involves altering the amino acid sequence of the wild-type acid phosphatase/phytase by introducing amino acid substitutions into SEQ. ID. No. 1 at positions 200, 207, and 211. Another embodiment of this method involves altering the amino acid sequence of the wild-type acid phosphatase/phytase having SEQ. ID. No. 1 by introducing at least one amino acid substitution which disrupts disulfide bond formation between Cys amino acid residues at positions 200 and 210.

Another aspect of this invention relates to an isolated DNA molecule which encodes the mutant acid phosphatase/phytase of the present invention. Also disclosed are recombinant DNA expression systems and host cells containing the DNA molecule of the present invention. These constructions can be used to recombinantly produce the mutant acid phosphatase/phytase of the present invention.

The invention also provides a basic molecular method that can be broadly applied to design mutant acid phosphatases/phytases derived from various source organisms, resulting in mutants with enhanced enzymatic properties such as greater thermostability and catalytic efficiency. This method includes identifying and isolating a gene of a wild-type enzyme and using this gene as the object of site-directed mutagenesis in order to enhance the enzyme's function and/or stability. One aspect of this invention is to use site-directed mutagenesis to make targeted mutations to the wild-type gene in order to add N-glycosylation sites to the wild-type enzyme and/or to alter the enzyme's physiochemical properties (e.g., increasing the net positive charge of the enzyme). In addition, targeted mutations can be made to the wild-type gene in order to eliminate certain disulfide bonds found in the final protein product, resulting in enhanced thermostability and catalytic function.

BRIEF DESCRIPTION OF THE DRAWINGS

FIG. 1 shows the nucleotide (SEQ. ID. No. 2) and the deduced amino acid (SEQ. ID. No. 1) sequence of the *E. coli* acid phosphatase/phytase (appA). Primers are underlined and indicated by arrows. The GH loop region (202–211) is in bold and C200 (in G helix) and C210 (in GH loop) form the unique disulfide bond in the a-domain. Substituted amino acids (A131, V134N, C200, D207, and S211) are underlined and in bold.

DETAILED DESCRIPTION OF THE INVENTION

Figure 2:
FIG. 2 shows an SDS-gel electrophoresis (15%) analysis of purified recombinant proteins expressed in *Pichia pastoris*. Thirty micrograms of protein was loaded per lane. Lane M, prestained marker (Biorad, kDa) (phosphorylase.b, 103; bovine serum albumin, 76; ovalbumin, 49; carbonic anhydrase, 33.2; soybean trypsin inhibitor, 28); Lane 1, Endo $H_f$ (endoglycosidase $H_f$); Lane 2, r-AppA (recombinant protein produced by appA in *Pichia pastoris*); Lane 3, r-AppA+Endo $H_f$; Lane 4, Mutant U; Lane 5, Mutant U+Endo $H_f$; Lane 6, Mutant R; Lane 7, Mutant R+Endo $H_f$; Lane 8, Mutant Y; Lane 9, Mutant Y+Endo $H_f$.

The present invention relates to an isolated mutant acid phosphatase/phytase which is produced by site-directed mutagenesis of a wild-type *Escherichia coli* acid phosphatase/phytase. According to one embodiment, the mutant acid phosphatase/phytase is made by introducing a plurality of targeted amino acid substitutions in a wild-type *Escherichia coli* acid phosphatase/phytase. In another embodiment, the mutant acid phosphatase/phytase is produced by introducing at least one amino acid substitution into the wild-type acid phosphatase/phytase in order to disrupt disulfide bond formation between Cys amino acid residues of the mutant acid phosphatase/phytase. The wild-type acid phosphatase/phytase has an amino acid sequence corresponding to SEQ. ID. No. 1 as follows:

```
Met Lys Ala Ile Leu Ile Pro Phe Leu Ser Leu Leu Ile Pro Leu
1               5                   10                  15
Thr Pro Gln Ser Ala Phe Ala Gln Ser Glu Pro Glu Leu Lys Leu
                20                  25                  30
Glu Ser Val Val Ile Val Ser Arg His Gly Val Arg Ala Pro Thr
                35                  40                  45
Lys Ala Thr Gln Leu Met Gln Asp Val Thr Pro Asp Ala Trp Pro
                50                  55                  60
Thr Trp Pro Val Lys Leu Gly Trp Leu Thr Pro Arg Gly Gly Glu
                65                  70                  75
Leu Ile Ala Tyr Leu Gly His Tyr Gln Arg Gln Arg Leu Val Ala
                80                  85                  90
Asp Gly Leu Leu Ala Lys Lys Gly Cys Pro Gln Pro Gly Gln Val
                95                  100                 105
Ala Ile Ile Ala Asp Val Asp Glu Arg Thr Arg Lys Thr Gly Glu
                110                 115                 120
Ala Phe Ala Ala Gly Leu Ala Pro Asp Cys Ala Ile Thr Val His
                125                 130                 135
Thr Gln Ala Asp Thr Ser Ser Pro Asp Pro Leu Phe Asn Pro Leu
                140                 145                 150
Lys Thr Gly Val Cys Gln Leu Asp Asn Ala Asn Val Thr Asp Ala
                155                 160                 165
Ile Leu Ser Arg Ala Gly Gly Ser Ile Ala Asp Phe Thr Gly His
                170                 175                 180
Arg Gln Thr Ala Phe Arg Glu Leu Glu Arg Val Leu Asn Phe Pro
                185                 190                 195
Gln Ser Asn Leu Cys Leu Lys Arg Glu Lys Gln Asp Glu Ser Cys
                200                 205                 210
Ser Leu Thr Gln Ala Leu Pro Ser Glu Leu Lys Val Ser Ala Asp
                215                 220                 225
Asn Val Ser Leu Thr Gly Ala Val Ser Leu Ala Ser Met Leu Thr
                230                 235                 240
Glu Ile Phe Leu Leu Gln Gln Ala Gln Gly Met Pro Glu Pro Gly
                245                 250                 255
Trp Gly Arg Ile Thr Asp Ser His Gln Trp Asn Thr Leu Leu Ser
                260                 265                 270
Leu His Asn Ala Gln Phe Tyr Leu Leu Gln Arg Thr Pro Glu Val
                275                 280                 285
Ala Arg Ser Arg Ala Thr Pro Leu Leu Asp Leu Ile Lys Thr Ala
                290                 295                 300
Leu Thr Pro His Pro Pro Gln Lys Gln Ala Tyr Gly Val Thr Leu
                305                 310                 315
Pro Thr Ser Val Leu Phe Ile Ala Gly His Asp Thr Asn Leu Ala
                320                 325                 330
Asn Leu Gly Gly Ala Leu Glu Leu Asn Trp Thr Leu Pro Gly Gln
                335                 340                 345
Pro Asp Asn Thr Pro Pro Gly Gly Glu Leu Val Phe Glu Arg Trp
                350                 355                 360
Arg Arg Leu Ser Asp Asn Ser Gln Trp Ile Gln Val Ser Leu Val
                365                 370                 375
Phe Gln Thr Leu Gln Gln Met Arg Asp Lys Thr Pro Leu Ser Leu
                380                 385                 390
Asn Thr Pro Pro Gly Glu Val Lys Leu Thr Leu Ala Gly Cys Glu
                395                 400                 405
Glu Arg Asn Ala Gln Gly Met Cys Ser Leu Ala Gly Phe Thr Gln
                410                 415                 420
Ile Val Asn Glu Ala Arg Ile Pro Ala Cys Ser Leu *
                425                 430
```

The wild-type acid phosphatase/phytase having the amino acid sequence according to SEQ. ID. No. 1 is encoded by the coding sequence of bases 187–1486 of the nucleotide sequence of SEQ. ID. No. 2 as follows:

```
   1 taa  gga gca gaa aca  ATG TGG TAT TTA  CTT TGG TTC GTC  GGC ATT

46 TTG  TTG ATG TGT TCG  CTC TCC ACC CTT  GTG TTG GTA TGG  CTG GAC

91 CCG  CGA TTG AAA AGT  T   aac gaa cgt  agg cct gat gcg  gcg cat 134 tag  cat cgc atc agg  caa tca ata atg  tca gat atg aaa  agc gga 179 aac  ata tcg ATG AAA  GCG ATC TTA ATC  CCA TTT TTA TCT  CTT CTG

224 ATT  CCG TTA ACC CCG  CAA TCT GCA TTC  GCT CAG AGT GAG  CCG GAG

269 CTG  AAG CTG GAA AGT  GTG GTG ATT GTC  AGC CGT CAT GGT  GTG CGT

314 GCC  CCA ACC AAG GCC  ACG CAA CTG ATG  CAG GAT GTC ACC  CCA GAC

359 GCA  TGG CCA ACC TGG  CCG GTA AAA CTG  GGT TGG CTG ACA  CCA CGC

404 GGT  GGT GAG CTA ATC  GCC TAT CTC GGA  CAT TAC CAA CGC  CAG CGT

449 CTG  GTG GCC GAC GGA  TTG CTG GCG AAA  AAG GGC TGC CCG  CAG CCT

494 GGT  CAG GTC GCG ATT  ATT GTC GAT GTC  GAC GAG CGT ACC  CGT AAA

539 ACA  GGC GAA GCC TTC  GCC GCC GGG CTG  GCA CCT GAC TGT  GCA ATA

584 ACC  GTA CAT ACC CAG  GCA GAT ACG TCC  AGT CCC GAT CCG  TTA TTT

629 ATT  CCT CTA AAA ACT  GGC GTT TGC CAA  CTG GAT AAC GCG  AAC GTG

674 ACT  GAC GCG ATC CTC  AGC AGG GCA GGA  GGG TCA ATT GCT  GAG TTT

719 ACC  GGG CAT CGG CAA  ACG GCG TTT CGC  GAA CTG GAA CGG  GTG CTT

764 AAT  TTT CCG CAA TCA  AAC TTG TGC CTT  AAA CGT GAG AAA  CAG GAC

809 GAA  AGC TGT TCA TTA  ACG CAG GCA TTA  CCA TCG GAA CTC  AAG GTG

854 AGC  GCC GAC AAT GTT  TCA TTA ACC GGT  GCG GTA AGC CTC  GCA TCA

899 ATG  CTG ACG GAA ATA  TTT CTG CTG CAA  CAA GCA CAG GGA  ATG CCG

944 GAG  CCG GGG TGG GGA  AGG ATC ACT GAT  TCA CAC CAG TGG  AAC ACC

989 TTG  CTA AGT TTG CAT  AAC GCG CAA TTT  TAT TTA CTA CAA  CGC ACG

1034 CCA  GAG GTT GCC CGC  AGT CGC GCC ACC  CCG TTA TTG GAT  TTG ATC

1079 AAG  ACA GCG TTG ACG  CCC CAT CCA CCG  CAA AAA CAG GCG  TAT GGT

1124 GTG  ACA TTA CCC ACT  TCA GTG CTG TTT  ATT GCC GGA CAC  GAT ACT

1169 AAT  CTG GCA AAT CTC  GGC GGC GCA CTG  GAG CTC AAC TGG  ACG CTT

1214 CCA  GGT CAG CCG GAT  AAC ACG CCG CCA  GGT GGT GAA CTG  GTG TTT

1259 GAA  CGC TGG CGT CGG  CTA AGC GAT AAC  AGC CAG TGG ATT  CAG GTT

1304 TCG  CTG GTC TTG CAG  ACT TTA CAG CAG  ATG CGT GAT AAA  ACG CCG

1349 CTA  TCA TTA AAT ACG  CCG CCC GGA GAG  GTG AAA CTG ACC  CTG GCA

1394 GGA  TGT GAA GAG CGA  AAT GCG CAG GGC  ATG TGT TCG TTG  GCC GGT

1439 TTT  ACG CAA ATC GTG  AAT GAA GCG CGC  ATA CCG GCG TGC  AGT TTG

1484 TAA
```

This acid phosphatase/phytase is derived from *E. coli*.

In producing the mutant acid phosphatase/phytase of the present invention, amino acid substitutions are made at positions 200, 207, and 211 of SEQ. ID. No. 1. It is particularly preferred to have the amino acid substitutions in the acid phosphatase/phytase of SEQ. ID. No. 1 be as follows: at position 200, be an Asn amino acid residue instead of a Cys amino acid residue; at position 207, be an Asn amino acid residue instead of an Asp amino acid residue; and at position 211, be an Asn amino acid residue instead of a Ser amino acid residue. As a result, the mutant acid phosphatase/phytase has an amino acid sequence of SEQ. ID. No. 3 as follows (the amino acid substitutions are underlined and in bold):

```
Met Lys Ala Ile Leu Ile Pro Phe Leu Ser Leu Leu Ile Pro Leu
1               5                   10                  15
Thr Pro Gln Ser Ala Phe Ala Gln Ser Glu Pro Glu Leu Lys Leu
            20                  25                  30
Glu Ser Val Val Ile Val Ser Arg His Gly Val Arg Ala Pro Thr
        35                  40                  45
Lys Ala Thr Gln Leu Met Gln Asp Val Thr Pro Asp Ala Trp Pro
    50                  55                  60
Thr Trp Pro Val Lys Leu Gly Trp Leu Thr Pro Arg Gly Gly Glu
65                  70                  75
Leu Ile Ala Tyr Leu Gly His Tyr Gln Arg Gln Arg Leu Val Ala
            80                  85                  90
Asp Gly Leu Leu Ala Lys Lys Gly Cys Pro Gln Pro Gly Gln Val
        95                  100                 105
Ala Ile Ile Ala Asp Val Asp Glu Arg Thr Arg Lys Thr Gly Glu
    110                 115                 120
Ala Phe Ala Ala Gly Leu Ala Pro Asp Cys Ala Ile Thr Val His
125                 130                 135
Thr Gln Ala Asp Thr Ser Ser Pro Asp Pro Leu Phe Asn Pro Leu
            140                 145                 150
Lys Thr Gly Val Cys Gln Leu Asp Asn Ala Asn Val Thr Asp Ala
        155                 160                 165
Ile Leu Ser Arg Ala Gly Gly Ser Ile Ala Asp Phe Thr Gly His
    170                 175                 180
Arg Gln Thr Ala Phe Arg Glu Leu Glu Arg Val Leu Asn Phe Pro
185                 190                 195
Gln Ser Asn Leu Asn Leu Lys Arg Glu Lys Gln Asn Glu Ser Cys
            200                 205                 210
Asn Leu Thr Gln Ala Leu Pro Ser Glu Leu Lys Val Ser Ala Asp
        215                 220                 225
Asn Val Ser Leu Thr Gly Ala Val Ser Leu Ala Ser Met Leu Thr
    230                 235                 240
Glu Ile Phe Leu Leu Gln Gln Ala Gln Gly Met Pro Glu Pro Gly
245                 250                 255
Trp Gly Arg Ile Thr Asp Ser His Gln Trp Asn Thr Leu Leu Ser
            260                 265                 270
Leu His Asn Ala Gln Phe Tyr Leu Leu Gln Arg Thr Pro Glu Val
        275                 280                 285
Ala Arg Ser Arg Ala Thr Pro Leu Leu Asp Leu Ile Lys Thr Ala
    290                 295                 300
Leu Thr Pro His Pro Pro Gln Lys Gln Ala Tyr Gly Val Thr Leu
305                 310                 315
Pro Thr Ser Val Leu Phe Ile Ala Gly His Asp Thr Asn Leu Ala
            320                 325                 330
Asn Leu Gly Gly Ala Leu Glu Leu Asn Trp Thr Leu Pro Gly Gln
        335                 340                 345
Pro Asp Asn Thr Pro Pro Gly Gly Glu Leu Val Phe Glu Arg Trp
    350                 355                 360
Arg Arg Leu Ser Asp Asn Ser Gln Trp Ile Gln Val Ser Leu Val
365                 370                 375
Phe Gln Thr Leu Gln Met Arg Asp Lys Thr Pro Leu Ser Leu
            380                 385                 390
Asn Thr Pro Pro Gly Glu Val Lys Leu Thr Leu Ala Gly Cys Glu
        395                 400                 405
Glu Arg Asn Ala Gln Gly Met Cys Ser Leu Ala Gly Phe Thr Gln
    410                 415                 420
Ile Val Asn Glu Ala Arg Ile Pro Ala Cys Ser Leu *
            425                 430
```

The mutant acid phosphatase/phytase of SEQ. ID. No. 3 has a molecular mass of 45 to 48 kDa, after deglycosylation, and has a specific phytase activity of 63 U/mg. The mature protein is represented by the amino acid sequence of amino acids 21–432 of SEQ. ID. No. 3.

Another aspect of the present invention involves producing a mutant acid phosphatase/phytase by inserting at least one amino acid substitution into the amino acid sequence of SEQ. ID. No. 1 in order to disrupt disulfide bond formation in the mutant acid phosphatase/phytase. In particular, targeted substitution of the Cys amino acid residue at positions 200 and/or 210 of SEQ. ID. No. 1 can be made in order to eliminate the disulfide bond between these residues.

The mutant acid phosphatase/phytase having an amino acid sequence according to SEQ. ID. No. 3 is encoded by the coding sequence of bases 187–1486 of the nucleotide sequence of SEQ. ID. No. 4 as follows (the codons for the substituted Asn residues at amino acid positions 200, 207, and 211 are underlined and in bold):

```
  1 taa   gga gca gaa aca   ATG TGG TAT TTA   CTT TGG TTC GTC   GGC ATT
 46 TTG   TTG ATG TGT TCG   CTC TCC ACC CTT   GTG TTG GTA TGG   CTG GAC
 91 CCG   CGA TTG AAA AGT   T   aac gaa cgt   agg cct gat gcg   gcg cat
134 tag   cat cgc atc agg   caa tca ata atg   tca gat atg aaa   agc gga
179 aac   ata tcg ATG AAA   GCG ATC TTA ATC   CCA TTT TTA TCT   CTT CTG
224 ATT   CCG TTA ACC CCG   CAA TCT GCA TTC   GCT CAG AGT GAG   CCG GAG
269 CTG   AAG CTG GAA AGT   GTG GTG ATT GTC   AGC CGT CAT GGT   GTG CGT
314 GCC   CCA ACC AAG GCC   ACG CAA CTG ATG   CAG GAT GTC ACC   CCA GAC
359 GCA   TGG CCA ACC TGG   CCG GTA AAA CTG   GGT TGG CTG ACA   CCA CGC
404 GGT   GGT GAG CTA ATC   GCC TAT CTC GGA   CAT TAC CAA CGC   CAG CGT
449 CTG   GTG GCC GAC GGA   TTG CTG GCG AAA   AAG GGC TGC CCG   CAG CCT
494 GGT   CAG GTC GCG ATT   ATT GTC GAT GTC   GAC GAG CGT ACC   CGT AAA
539 ACA   GGC GAA GCC TTC   GCC GCC GGG CTG   GCA CCT GAC TGT   GCA ATA
584 ACC   GTA CAT ACC CAG   GCA GAT ACG TCC   AGT CCC GAT CCG   TTA TTT
629 ATT   CCT CTA AAA ACT   GGC GTT TGC CAA   CTG GAT AAC GCG   AAC GTG
674 ACT   GAC GCG ATC CTC   AGC AGG GCA GGA   GGG TCA ATT GCT   GAC TTT
```

-continued

| | | | | |
|---|---|---|---|---|
| 719 ACC | GGG CAT CGG CAA | ACG GCG TTT CGC | GAA CTG GAA CGG | GTG GTT |
| 764 AAT | TTT CCG CAA TCA | AAC TTG AAC CTT | AAA CGT GAG AAA | CAG AAT |
| 809 GAA | AGC TGT AAC TTA | ACG CAG GCA TTA | CCA TCG GAA CTC | AAG GTG |
| 854 AGC | GCC GAC AAT GTT | TCA TTA ACC GGT | GCG GTA AGC CTC | GCA TCA |
| 899 ATG | CTG ACG GAA ATA | TTT CTC CTG CAA | CAA GCA CAG GGA | ATG CCG |
| 944 GAG | CCG GGG TGG GGA | AGG ATC ACT GAT | TCA CAC CAG TGG | AAC ACC |
| 989 TTG | CTA AGT TTG CAT | AAC GCG CAA TTT | TAT TTA CTA CAA | CGC ACG |
| 1034 CCA | GAG GTT GCC CGC | AGT CGC GCC ACC | CCG TTA TTG GAT | TTG ATC |
| 1079 AAG | ACA GCG TTG ACG | CCC CAT CCA CCG | CAA AAA CAG GCG | TAT GGT |
| 1124 GTG | ACA TTA CCC ACT | TCA GTG CTG TTT | ATT GCC GGA CAC | GAT ACT |
| 1169 AAT | CTG GCA AAT CTC | GGC GGC GCA CTG | GAG CTC AAC TGG | ACG CTT |
| 1214 CCA | GGT CAG CCG GAT | AAC ACG CCG CCA | GGT GGT GAA CTG | GTG TTT |
| 1259 GAA | CGC TGG CGT CGG | CTA AGC GAT AAC | AGC CAG TGG ATT | CAG GTT |
| 1304 TCG | CTG GTC TTC CAG | ACT TTA CAG CAG | ATG CGT GAT AAA | ACG CCG |
| 1349 CTA | TCA TTA AAT ACG | CCG CCC GGA GAG | GTG AAA CTG ACC | CTG GCA |
| 1394 GGA | TGT GAA GAG CGA | AAT GCG CAG GGC | ATG TGT TCG TTG | GCC GGT |
| 1439 TTT | ACG CAA ATC GTG | AAT GAA GCG CGC | ATA CCG GCG TGC | AGT TTG |
| 1484 TAA | | | | |

One embodiment of the present invention involves the insertion of the mutant acid phosphatase/phytase gene into an expression vector system, using recombinant DNA technology well known in the art. This enables one to express this gene in a host cell, allowing for the production and purification of the acid phosphatase/phytase for use in compositions, such as for animal feed.

The DNA of the mutant acid phosphatase/phytase gene can be isolated and/or identified using DNA hybridization techniques. Nucleic acid (DNA or RNA) probes of the present invention will hybridize to a complementary nucleic acid under stringent conditions. Less stringent conditions may also be selected. Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and for DNA:RNA hybridization may be calculated using the following equation:

$$T_m = 79.8° \text{C.} + (18.5 \times \text{Log}[\text{Na}^+]) + (58.4° \text{C.} \times \%[G+C]) - (820/\text{\#bp in duplex}) - (0.5 \times \% \text{ formamide})$$

*Promega Protocols and Applications Guide*, 2d ed., Promega Corp., Madison, Wis. (1991), which is hereby incorporated by reference. Nonspecific binding may also be controlled using any one of a number of known techniques such as, for example, blocking the membrane with protein-containing solutions, addition of heterologous RNA, DNA, and SDS to the hybridization buffer, and treatment with RNase.

Generally, suitable stringent conditions for nucleic acid hybridization assays or gene amplification detection procedures are as set forth above or as identified in Southern, "Detection of Specific Sequences Among DNA Fragments Separated by Gel Electrophoresis," *J. Mol. Biol.*, 98:503–17 (1975), which is hereby incorporated by reference. For example, conditions of hybridization at 42° C. with 5X SSPE and 50% formamide with washing at 50° C. with 0.5X SSPE can be used with a nucleic acid probe containing at least 20 bases, preferably at least 25 bases or more preferably at least 30 bases. Stringency may be increased, for example, by washing at 55° C. or more preferably 60° C. using an appropriately selected wash medium having an increase in sodium concentration (e.g., 1X SSPE, 2X SSPE, 5X SSPE, etc.). If problems remain with cross-hybridization, further increases in temperature can also be selected, for example, by washing at 65° C., 70° C., 75° C., or 80° C. By adjusting hybridization conditions, it is possible to identify sequences having the desired degree of homology (i.e., greater than 80%, 85%, 90%, or 95%) as determined by the TBLASTN program (Altschul, S. F., et al., "Basic Local Alignment Search Tool," *J. Mol. Biol.* 215:403–410 (1990), which is hereby incorporated by reference) on its default setting.

A preferred method of detecting the mutant acid phosphatase/phytase of the present invention is by using the methods known in the art as ligase detection reaction (LDR) and ligase chain reaction (LCR), as described in Barany, "Genetic Disease Detection and DNA Amplification Using Cloned Thermostable Ligase," *Proc. Natl. Acad. Sci. USA* 88(1):189–193 (1991), which is hereby incorporated by reference.

The DNA molecule of the present invention can be expressed in any prokaryotic or eukaryotic expression system by incorporation of the DNA molecule in the expression system in proper orientation and correct reading frame. A variety of host-vector systems may be utilized to express the protein-encoding sequence(s). Preferred vectors include a viral vector, plasmid, cosmid or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used. For example, a DNA molecule in accordance with the present invention is spliced in frame with a transcriptional enhancer element.

Preferred hosts for expressing the DNA molecule of the present invention include fungal cells, including species of yeast or filamentous fungi, may be used as host cells in accordance with the present invention. Preferred yeast host cells include different strains of *Saccharomyces cerevisiae*. Other yeasts like *Kluyveromyces, Torulaspora,* and *Schizosaccharomyces* can also be used. In a preferred embodiment, the yeast strain used to overexpress the protein is *Saccharomyces cerevisiae*. Preferred filamentous fungi host cells include *Aspergillus* and *Neurospora*. A more preferred strain of *Aspergillus* is *Aspergillus niger.*

In another preferred embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera *Pichia, Hansenula, Torulopsis, Candida,* and *Karwinskia*. These yeast genera can use methanol as a sole carbon source. In a more preferred embodiment, the methylotrophic yeast strain is *Pichia pastoris*.

Purified protein may be obtained by several methods. The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The present invention also provides a yeast strain having a heterologous gene which encodes a protein or polypeptide with phytase activity. The heterologous gene should be functionally linked to a promoter capable of expressing phytase in yeast.

Yet another aspect of the invention is a vector for expressing phytase in yeast. The vector carries a gene from a non-yeast organism which encodes a protein or polypeptide with phytase activity. The phytase gene can be cloned into any vector which replicates autonomously or integrates into the genome of yeast. The copy number of autonomously replicating plasmids, e.g. YEp plasmids, may be high, but their mitotic stability may be insufficient (Bitter et al., "Expression and Secretion Vectors for Yeast," *Meth. Enzymol.* 153:516–44 (1987), which is hereby incorporated by reference). They may contain the 2 mu-plasmid sequence responsible for autonomous replication, and an *E. coli* sequence responsible for replication in *E. coli*. The vectors preferably contain a genetic marker for selection of yeast transformants, and an antibiotic resistance gene for selection in *E. coli*. The episomal vectors containing the ARS and CEN sequences occur as a single copy per cell, and they are more stable than the YEp vectors. Integrative vectors are used when a DNA fragment is integrated as one or multiple copies into the yeast genome. In this case, the recombinant DNA is stable and no selection is needed (Struhl et al., "High-Frequency Transformation of Yeast: Autonomous Replication of Hybrid DNA Molecules," *Proc. Nat'l Acad. Sci. USA* 76:1035–39 (1979); Powels et al., *Cloning Vectors, I–IV, et seq.* Elsevier, (1985); and Sakai et al., "Enhanced Secretion of Human Nerve Growth Factor from *Saccharomyces Cerevisiae* Using an Advanced δ-Integration System," *Biotechnology* 9:1382–85 (1991), which are hereby incorporated by reference). Some vectors have an origin of replication, which functions in the selected host cell. Suitable origins of replication include 2μ, ARS1, and 25 μM. The vectors have restriction endonuclease sites for insertion of the fusion gene and promoter sequences, and selection markers. The vectors may be modified by removal or addition of restriction sites, or removal of other unwanted nucleotides.

The phytase gene can be placed under the control of any promoter (Stetler et al., "Secretion of Active, Full- and Half-Length Human Secretory Leukocyte Protease Inhibitor by *Saccharomyces cerevisiae,*" *Biotechnology* 7:55–60, (1989), which is hereby incorporated by reference). One can choose a constitutive or regulated yeast promoter. Suitable promoter sequences for yeast vectors include, among others, promoters for metallothionein, 3-phosphoglycerate kinase (Hitzeman et al., *J. Biol. Chem.* 255:2073 (1980), which is hereby incorporated by reference) or other glycolytic enzymes (Hess et al., *J. Adv. Enzyme Reg.* 7:149 (1968); and Holland et al., *Biochem.* 17:4900, (1978), which are hereby incorporated by reference), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in EP A-73,657 to Hitzeman, which is hereby incorporated by reference. Another alternative is the glucose-repressible ADH2 promoter described by Russell et al., *J. Biol. Chem.* 258:2674 (1982) and Beier et al., *Nature* 300:724 (1982), which are hereby incorporated by reference.

One can choose a constitutive or regulated yeast promoter. The strong promoters of e.g., phosphoglycerate kinase (PGK) gene, other genes encoding glycolytic enzymes, and the alpha-factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP 150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter, can be used, but in this case the yeast strain has to be transformed with a gene encoding the respective polymerase. For transcription termination, the HSP 150 terminator, or any other functional terminator is used. Here, promoters and terminators are called control elements. The present invention is not restricted to any specific vector, promoter, or terminator.

The vector may also carry a selectable marker. Selectable markers are often antibiotic resistance genes or genes capable of complementing strains of yeast having well characterized metabolic deficiencies, such as tryptophan or histidine deficient mutants. Preferred selectable markers include URA3, LEU2, HIS3, TRP1, HIS4, ARG4, or antibiotic resistance genes.

The vector may also have an origin of replication capable of replication in a bacterial cell. Manipulation of vectors is more efficient in bacterial strains. Preferred bacterial origin of replications are ColE1, Ori, or oriT.

Preferably, the protein or polypeptide with phytase activity is secreted by the cell into growth media. This allows for higher expression levels and easier isolation of the product. The protein or polypeptide with phytase activity is coupled to a signal sequence capable of directing the protein out of the cell. Preferably, the signal sequence is cleaved from the protein.

A leader sequence either from the yeast or from phytase genes or other sources can be used to support the secretion of expressed phytase enzyme into the medium. The present invention is not restricted to any specific type of leader sequence or signal peptide.

Suitable leader sequences include the yeast alpha factor leader sequence, which may be employed to direct secretion of the phytase. The alpha factor leader sequence is often inserted between the promoter sequence and the structural gene sequence (Kurjan et al., Cell 30:933, (1982); Bitter et al., Proc. Natl. Acad. Sci. USA 81:5330, (1984); U.S. Pat. No. 4,546,082; and European published patent application No. 324,274, which are hereby incorporated by reference). Another suitable leader sequence is the S. cerevisiae MF alpha 1 (alpha-factor) is synthesized as a prepro form of 165 amino acids comprising signal-or prepeptide of 19 amino acids followed by a "leader" or propeptide of 64 amino acids, encompassing three N-linked glycosylation sites followed by (LysArg(Asp/Glu, Ala)2-3 alpha-factor)4 (Kuijan, et al., Cell 30:933–43 (1982), which is hereby incorporated by reference). The signal-leader part of the preproMF alpha 1 has been widely employed to obtain synthesis and secretion of heterologous proteins in S. cerivisiae. Use of signal/leader peptides homologous to yeast is known from: U.S. Pat. No. 4,546,082; European Patent Applications Nos. 116,201, 123,294, 123,544, 163,529, and 123,289; and DK Patent Application No. 3614/83, which are hereby incorporated by reference. In European Patent Application No. 123,289, which is hereby incorporated by reference, utilization of the S. cerevisiae a-factor precursor is described whereas WO 84/01153, which is hereby incorporated by reference, indicates utilization of the Saccharomyces cerevisiae invertase signal peptide, and German Patent Application DK 3614/83, which is hereby incorporated by reference, indicates utilization of the Saccharomyces cerevisiae PHO5 signal peptide for secretion of foreign proteins.

The alpha-factor signal-leader from Saccharomyces cerevisiae (MF alpha 1 or MF alpha 2) may also be utilized in the secretion process of expressed heterologous proteins in yeast (U.S. Pat. No. 4,546,082; European Patent Applications Nos. 16,201, 123,294, 123,544, and 163,529, which are hereby incorporated by reference). By fusing a DNA sequence encoding the S. cerevisiae MF alpha 1 signal/leader sequence at the 5' end of the gene for the desired protein, secretion and processing of the desired protein was demonstrated. The use of the mouse salivary amylase signal peptide (or a mutant thereof) to provide secretion of heterologous proteins expressed in yeast has been described in Published PCT Applications Nos. WO 89/02463 and WO 90/10075, which are hereby incorporated by reference.

U.S. Pat. No. 5,726,038 describes the use of the signal peptide of the yeast aspartic protease 3, which is capable of providing improved secretion of proteins expressed in yeast. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929 (1978), which is hereby incorporated by reference. The Hinnen et al. protocol selects for Trp transformants in a selective medium, wherein the selective medium consists of 0.67% yeast nitrogen base, 0.5% casamino acids, 2% glucose, 10 µg/ml adenine and 20 µg/ml uracil.

The gene may be maintained in a stable expression vector, an artificial chromosome, or by integration into the yeast host cell chromosome. Integration into the chromosome may be accomplished by cloning the phytase gene into a vector which will recombine into a yeast chromosome. Suitable vectors may include nucleotide sequences which are homologous to nucleotide sequences in the yeast chromosome. Alternatively, the phytase gene may be located between recombination sites, such as transposable elements, which can mobilize the gene into the chromosome.

Another aspect of the present invention relates to improving the enzymatic properties of a wild-type acid phosphatase/phytase. This is desirably achieved by altering the amino acid sequence of the wild-type acid phosphatase/phytase at positions 200, 207, and 211 as described above. For example, these modifications cause the acid phosphatase/phytase to have improved thermostability. Alternatively, the improved enzymatic property is phytase activity at a pH range of between about pH 3.5 to about pH 5.5.

While the phytase enzyme produced in a yeast system released phytate-P from corn and soy as effectively as the currently commercial phytase, it appeared to be more thermostable. This phytase overexpression system in yeast can be used to provide thermostable phytase for use in the food and feed industries.

The improved acid phosphatase/phytase of this invention can be used in animal feed to improve the digestion of phosphate by such simple-stomached animals as poultry, swine, pre-rulninant calves, zoo animals, and pets (e.g., cats and dogs). The present invention would decrease the need for supplementing animal feed with large amounts of inorganic phosphate, resulting in a less expensive form of animal feed and one that is less concentrated with the non-renewable form of phosphate. Since the present invention enhances the ability of simple-stomached animals to absorb phosphate, the fecal waste of these animals will contain less unutilized phytate-phosphate, which decreases the amount of phosphate pollution.

In making the animal feed composition of the present invention, the mutant acid phosphatase/phytase is combined with a raw plant material and then processed into a pellet or powder form. The raw plant material may include various combinations of a number of plants and/or plant by-products commonly used in animal feed, including plants such as maize, soybean, wheat, rice, cotton seed, rapeseed, sorghum, and potato. In addition, the animal feed composition may be fortified with various vitamins, minerals, animal protein, and antibiotics. One embodiment of the animal feed composition includes a mixture of appropriate concentrations of the mutant acid phosphatase/phytase, an energy source(s) (e.g., maize, wheat), a protein source(s) (e.g., soybean, rice, cottonseed meal, rapeseed meal, sorghum meal), and vitamin/mineral supplements. In particular, the amount of the mutant acid phosphatase/phytase would be 300–1,000 Units/kg of feed. One example of a typical animal feed composition would include 50–70% maize, 20–30% soybean, approximately 1% vitamin and mineral supplements, and an appropriate amount of mutant acid phosphatase/phytase.

In addition, the mutant acid phosphatase/phytase of the present invention could be used to enhance human nutrition, particularly by increasing the uptake of such minerals as zinc and iron. By adding the mutant acid phosphatase/phytase to the diets of humans, various problems arising from nutrient deficiencies, such as stunted growth and mental retardation in children, could be treated and avoided.

The invention also provides a basic molecular method that can be broadly applied to design mutant acid phosphatases/phytases derived from various source organisms, resulting in mutants with enhanced enzymatic properties such as greater thermostability and catalytic efficiency. This method includes identifying and isolating a gene of a wild-type enzyme and using this gene as the object of site-directed mutagenesis in order to enhance the enzyme's function and/or stability. One aspect of this invention is to use site-directed mutagenesis to make targeted mutations to the wild-type gene in order to add N-glycosylation sites to the wild-type enzyme and/or to alter the enzyme's physiochemical properties (e.g., increasing the net positive charge of the enzyme). In addition, targeted mutations can be made to the wild-type gene in order to eliminate certain disulfide bonds found in the final protein product, resulting in enhanced thermostability and catalytic function.

EXAMPLES

Example 1

Sequence Analysis for Designing Mutations

The criteria for designing mutations to enhance glycosylation of the AppA enzyme were 1) the potential glycosylation site should have 25% or greater solvent accessibility, and 2) the site should be easily engineered by a single residue change to give an N-linked glycosylation motif (Asn-X-Ser or Asn-X-Thr, where X is not a proline). Initially, in the absence of a crystal structure for the AppA enzyme, the crystal structure of rat acid phosphatase (35% sequence identity) (Schneider, G. et al., *EMBO J.* 12:2609–15 (1993), which is hereby incorporated by reference) was used to calculate accessibilities as follows. First, the AppA enzyme and rat acid phosphatase were aligned to several closely related phosphatases/phytases using the multi-sequence alignment program PIMA (Smith, R. et al., *Protein Engineering* 5:35–41 (1992), which is hereby incorporated by reference). The aligned sequences included: human prostatic acid phosphatase precursor (GeneBank Accession No. P15309); *Caenorhabditis elegans* histidine acid phosphatase (GeneBank Accession No. Z68011); *Aspergillus fumigatus* phytase (GeneBank Accession No. U59804); *Pichia angusta* repressible acid phosphatase (GeneBank Accession No. AF0511611); rat acid phosphatase (GeneBank Accession No. 576257), and *E. coli* appA (GeneBank Accession No. M58708). Next, the solvent accessible surface of all of the amino acids of rat phosphatase was determined using the program DSSP (definition of secondary structure of proteins) (Kabsch, W. et al., *Biopolymers* 22:2577–637 (1983), which is hereby incorporated by reference), converting these values to percent accessibility by dividing the total surface area of the corresponding amino acid as it has been previously described (Eisenberg, D. et al., *Chemica Scripta* 29A, 217–221 (1989), which is hereby incorporated by reference). Only residues greater than 25% solvent were considered accessible. Values were assigned to the corresponding amino acids in the AppA enzyme based on the sequence alignment described above, under the assumption that the overall structure of rat acid phosphatase and the AppA enzyme would be conserved. Finally, the putative solvent accessible residues were examined to determine which could be easily converted to an N-glycosylation site by point mutation. Out of 31 potential sites, 5 were selected that best fit the desired criteria. An additional mutation C200N was incorporated using primer P2 designed for another appA mutagenesis study. From the alignment performed, the mutation C200N is in a gapped region and C200 is involved with C210 (labeled as C178/C188 by Lim et al., *Nat. Struct. Biol.* 7:108–13 (2000), which is hereby incorporated by reference) in forming a unique disulfide bond between helix G and the GH loop (an unorganized configuration between the G and H helices) in the α-domain of the protein (Lim et al., *Nat. Struct. Biol.* 7:108–13 (2000), which is hereby incorporated by reference). Correspondingly, 6 PCR primers were designed: E2 and K2 for amplifying the wild-type sequence of appA (Dassa, J. et al., *J. Bacteriol.* 172:5497–500 (1990), which is hereby incorporated by reference) and the others for developing four mutants (Table 1 and FIG. 1). All the primers were synthesized by the Cornell University Oligonucleotide Synthesis Facility (Ithaca, N.Y.).

TABLE 1

Modified primers and index of surface solvent accessibility for mutations

| Primer[1] | Position[2] | Primer sequence[3] | Modification[4] | Accessibility[5] (%) |
|---|---|---|---|---|
| E2 (f) | 241–264 | 5' GGAATTCGCTCAGAGCCGGA 3' (SEQ. ID. No. 5) | EcoR1 restriction site | — |
| A1 (r) | 565–592 | 5' CTGGGTATG<u>GTT</u>GGTTAT<u>ATT</u>ACAGTCAGGT 3' (SEQ. ID. No. 6) | A131N V134N | 1.05 0.55 |

TABLE 1-continued

Modified primers and index of surface solvent accessibility for mutations

| Primer[1] | Position[2] | Primer sequence[3] | Modification[4] | Accessibility[5] (%) |
|---|---|---|---|---|
| P2 (f) | 772–795 | 5' CAAACTTGAACCTTA AACGTGAG 3' (SEQ. ID. No. 7) | C200N | nd |
| P3 (r) | 796–825 | 5' CCTGCGTTAAGTTAC AGCTTTCATTCTGTTT 3' (SEQ. ID. No. 8) | D207N | 0.63 |
|  |  |  | S211N | 0.65 |
| K2 (r) | 1469–1491 | 5' GGGGTACCTTACAAA CTGCACG 3' (SEQ. ID. No. 9) | KpnI restriction site | — |

[1]f forward; r, reverse.
[2]Nucleotide position based on the E. coli periplasmic pH 2.5 acid phosphatase (GeneBank Accession No. M58708).
[3]Underlined nucleotides were substituted.
[4]Amino-acid mutation or restriction site added. The coding region starts at the codon 20 and ends at the codon 432. Amino acids A131, V134, C200, D207, and S211 are labeled A109, V112, C178, D185, and S189 by Lim et al. (Lim et al., Nat. Struct. Biol. 7:108–13 (2000), which is hereby incorporated by reference).
[5]Percentage of amino acid surface solvent accessibility (Smith, R. et al., Protein Engineering 5:35–41 (1992); Kabsch, W. et al., Biopolymers 22:2577–637 (1983), which are hereby incorporated by reference); nd, not determined.

Example 2

Construction of Mutants by PCR

The *E. coli* appA mutants were constructed using the megaprimer site-directed mutagenesis method adapted from previous studies (Seraphin, B. et al., *Nucl. Acids Res.* 24:3276–77 (1996); Smith, A. M. et al., *BioTechniques* 22:438–39 (1997), which are hereby incorporated by reference). To amplify the intact coding region of appA, the PCR was set up in a 50 µl final volume containing 200 ng DNA of appA inserted in a pAPPA1 plasmid isolated from *E. coli* strain BL21 (Dassa, J. et al., *J. Bacteriol.* 172:5497–500 (1990), which is hereby incorporated by reference), 50 pmol of each primer E2 and K2, 5 U of AmpliTaq DNA polymerase (Perkin Elmer, Norwalk, Conn.), 10 mM Tris-HCl pH 8.3, 50 mM KCl, 12.5 mM MgCl2, and 200 mM each dNTPs (Promega Corp., Madison, Wis.). The reaction was performed using the GeneAmp PCR system 2400 (Perkin Elmer), and included 1 cycle at 94° C. (3 min), 30 cycles of [94° C. (0.5 min), 54° C. (1 min) and 72° C. (1.5 min)] and 1 cycle at 72° C. (10 min). Megaprimers for mutants were produced in a separated round of PCR (Table 2).

TABLE 2

E. coli appA mutant denomination and construction

| | | Construct[1] | Size bp | No. glycosylation |
|---|---|---|---|---|
| Mutants | R | E2A1P3K2 | 1350 | 7 |
|  | U | E2P2P3K2 | 1350 | 5 |
|  | Y | E2A1P2P3K2 | 1350 | 7 |

TABLE 2-continued

E. coli appA mutant denomination and construction

| | | Construct[1] | Size bp | No. glycosylation |
|---|---|---|---|---|
| Wild type | r-AppA | E2K2 | 1350 | 3 |

[1]See Table 1 for primer denomination.

The first mutagenic PCR reaction (100 µl) was performed as described above, using 4 µl of the intact appA PCR reaction mixture and the respective modified primers listed in Table 1. All megaprimer PCR products were resolved in a 1.5% low melting agarose (Gibco BRL, Grand Island, N.Y.) gel electrophoresis. The expected fragments were excised and eluted with GENECLEAN II kit (Bio101, Vista, Calif.). The final mutagenic PCR reaction (100 µl) was set up as described above, using 4 µl of the appA PCR product and varying concentrations of the purified megaprimer (50 ng to 4 µg), depending on its size. Five thermal cycles were set up at 94° C. for 1 min and 70° C. for 2 min. While at 70° C., 1 µmol of forward primer and 2 U of AmpliTaq DNA polymerase were added and gently mixed with the reaction, and thermal cycling continued for 25 times at 94° C. for 1 min, 56° C. for 1 min and 70° C. for 1.5 min.

Example 3

Subcloning and Expression

*E. coli* strain TOP10F' (Invitrogen, San Diego, Calif.) was used as an initial host. The PCR fragments were purified and cloned into pGEMT-Easy vector (Promega) according to the manufacturer's instructions. EcoRi digestion of the isolated plasmid DNA was used to screen for positive transformants. The resulting inserts were cloned into pPICZαA (Kit Easy-Select, Invitrogen) at the EcoRi site and transformed into TOP10F' cells plated on LB (Luria-Bertani) medium containing 25 µg/ml Zeocin. Colonies with desired inserts in the correct orientations were selected using SalI or BstXI restriction digestions of plasmid DNA. *P. pastoris* strain X33 (Mut+His+) was used as the host for protein expression (Invitrogen) and grown in YPD (yeast extract peptone dextrose medium) liquid medium prior to electroporation. Two µg of plasmid DNA were linearized using restriction enzyme BglII or PmeI and then transformed into X33 according to the manufacturer's instructions (Invitrogen). After selected transformants were incubated in minimal media with glycerol (GMGY) for 24 h, 0.5% methanol medium (GMMY) was used to induce protein expression.

Example 4

Enzyme Purification and Biochemical Characterization

The expressed r-AppA and mutant enzymes in the medium supernatant were subjected to a two-step ammonium sulfate precipitation (25% and 75%) as previously described (Rodriguez, E. et al., *Biochem. Biophys. Res. Commun.* 257:117–23 (1999), which is hereby incorporated by reference). The suspension of the first round was centrifuged at 4° C., 25,000×g for 20 min. The pellet of the second round was suspended in 10 ml and dialyzed overnight against 25 mM Tris-HCl, pH 7. After dialysis, the protein extract was loaded onto a DEAE (diethylaminoethyl)-Sepharose column (Sigma, St. Louis, Mo.) equilibrated with 25 mM Tris-HCl, pH 7. The bound protein was eluted with 1 M NaCl in 25 mM Tris-CHl, pH 7. Those three fractions exhibiting the highest activities were pooled and dialyzed against 25 mM Tris-HCl, pH 7.5 for the following analysis. Phytase activity was measured using sodium phytate as the substrate (Rodriguez, E. et al., *Biochem. Biophys. Res. Commun.* 257:117–23 (1999); Piddington, C. S. et al., *Gene* 133:55–62 (1993), which are hereby incorporated by reference). The enzyme was diluted in 0.25 M glycine-HCl, pH 2.5, and an equal volume of substrate solution containing 11 mM sodium phytate (Sigma) was added. After incubation of the sample for 15 min at 37° C., the reaction was stopped by addition of an equal volume of 15% trichloroacetic acid. Free inorganic phosphorus was measured at 820 nm after 0.2 ml of the sample was mixed with 1.8 ml of $H_2O$ and 2 ml of a solution containing 0.6 M $H_2SO_4$, 2% ascorbic acid, and 0.5% ammonium molybdate, followed by incubation for 20 min at 50° C. One phytase unit was defined as the amount of activity that releases 1 μmol of inorganic phosphorus from sodium phytate per minute at 37° C. The final concentrations of sodium phytate used for the enzyme kinetics were: 0.1, 0.25, 0.5, 0.75, 1, 2.5, 10, and 25 mM. Acid phosphatase activity was assayed using pNPP (Sigma) at a final concentration of 25 mM (Smith, R. et al., *Protein Engineering* 5:35–41 (1992), which is hereby incorporated by reference). To 50 μl of enzyme (40 nmol), 850 μl of 250 mM glycine-HCl, pH 2.5, were added. After 5 min of incubation at 37° C., 100 μl of pNPP was added. The released p-nitrophenol was measured at 405 nm after 0.1 ml of the sample was mixed with 0.9 ml of 1 M NaOH and incubated for 10 min. The final concentrations of pNPP used for the enzyme kinetics were: 0.1, 0.2, 0.75, 1, 2.5, 10, and 25 mM. One unit of acid phosphatase/phytase activity was defined as the amount of enzyme catalyzing the formation of 1 μmol of p-nitrophenol per minute. Before the thermostability assay, the enzyme (2 mg/ml) was diluted 1:400 in 0.2 M glycine-HCl, pH 2.5. The diluted samples were incubated for 15 min at 25, 55, 80, and 90° C. After the samples were cooled on ice for 30 min, their remaining phytase activies were measured as described above. Deglycosylation of purified enzymes was done by incubating 100 μg of total protein with 0.5 IU endoglycosidase $H_f$ (Endo $H_f$) for 4 h at 37° C. according to the manufacturer's instructions (New England Biolabs, Beverly, Mass.). Sodium dodecyl sulfate-polyacrylamide gel electrophoresis (SDS-PAGE), 15% (w/v) gel was performed as previously described (Laemmli, U. K., *Nature* 227:680–85 (1970), which is hereby incorporated by reference). Protein concentrations were determined using the Lowry method (Lowry, O. H. et al., *J. Biol. Chem.* 193: 265–75 (1951), which is hereby incorporated by reference).

Data were analyzed using SAS (release 6.04, SAS institute, Cary, N.C., USA).

Example 5

Effects of Site-Directed Mutagenesis on Phytase Expression and Glycosylation

Genomic DNA from each yeast transformant was extracted to amplify the desired mutated appA by PCR (polymerase chain reaction) using E2 and K2 primers. All the desired mutations were confirmed by sequencing. For each mutant, 24 colonies were analyzed for phytase activity at various times after induction. All of the three mutants, Mutant R, Mutant U, and Mutant Y, along with r-AppA, were expressed and secreted, resulting in a time-dependent accumulation of extracellular phytase activity that reached plateau at 96 h after methanol induction. The plateau activity in the medium supernatant was 35, 175, 57, and 117 U/mL, respectively (Table 3). Yeast X33 transformed with the expression vector pPICZαA was used as a control and did not give any activity or phytase protein in SDS-PAGE. On the purified protein basis, Mutant U had the highest specific phytase activity, 63 U/mg, followed by Mutant Y, r-AppA and Mutant R (51, 41 and 32 U/mg protein, respectively). The protein yield recovered after purification was 654, 324, 688 and 425 mg/L for the Mutants U and Y, r-AppA and Mutant R, respectively (Table 3).

TABLE 3

Phytase yield and specific activity of r-AppA and the three mutants

| Protein | Phytase activity[1] | Protein yield[2] | Specific activity[3] | |
|---|---|---|---|---|
| | | | −Endo $H_f$ | +Endo $H_f$ |
| r-AppA | 117 ± 15 | 688 ± 44 | 41 ± 3 | 37 ± 4 |
| R | 35 ± 4 | 425 ± 26 | 32 ± 2 | 29 ± 2 |
| U | 175 ± 19 | 654 ± 39 | 63 ± 4* | 65 ± 5* |
| Y | 57 ± 8 | 324 ± 18 | 51 ± 5 | 46 ± 6 |

[1]Phytase activity (U/ml) in GMMY media after 96 h of culture.
[2]Protein yield (milligrams of purified protein per liter of culture).
[3]Specific phytase activity (units per milligram of purified protein).
*Indicates significant difference (P < 0.05) versus the r-AppA control.
Results are representative of three experiments.

In SDS-PAGE, the band size of the purified r-AppA was 50–56 kDa, while that of Mutant R was 68–70 kDa and that of Mutant Y was 86–90 kDa (FIG. 2). This gave an enhancement of the glycosylation level from 14% in r-AppA to 48% in Mutant R and 89% in Mutant Y. The level of glycosylation in Mutant U appeared equivalent to that of r-AppA. All of these recombinant enzymes showed similar molecular mass, 45 to 48 kDa, after deglycosylation by Endo $H_f$. Deglycosylation did not significantly affect the specific activity for all the mutants or r-AppA (Table 3). However, treating these purified proteins with both β-mercaptoethanol and Endo $H_f$ caused a complete loss of phytase activity.

Example 6

Figure 3:
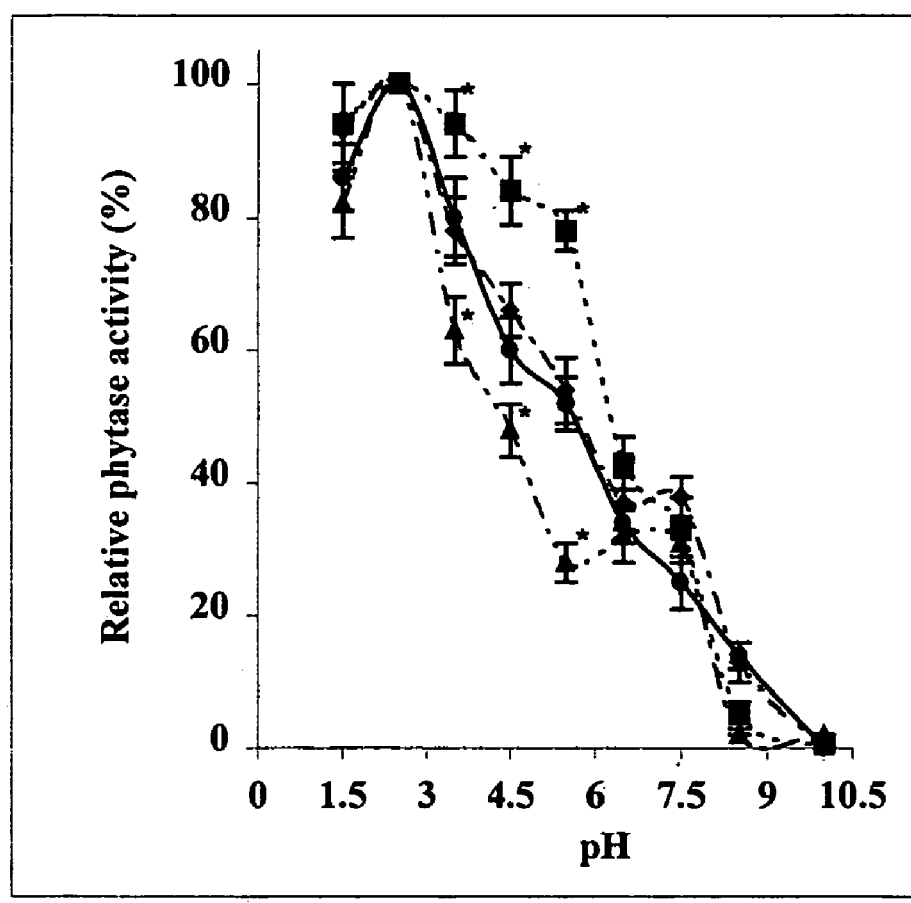
FIG. 3 shows the pH dependence of the enzymatic activity at 37° C. of the purified r-AppA (λ) and Mutants (U, ■; Y, σ, R, ♥) using sodium phytate as a substrate. The maximal activity for each mutant and r-AppA was defined as 100%. Buffers: pH 1.5–3.5, 0.2 M glycine-HCl; pH 4.5–7.5, 0.2 M sodium citrate; pH 8.5–11, 0.2 M Tris-HCl. Asterisks indicate significant differences (P<0.05) between r-AppA and other mutants. Results are expressed as the mean±SE from three experiments.
Figure 4:
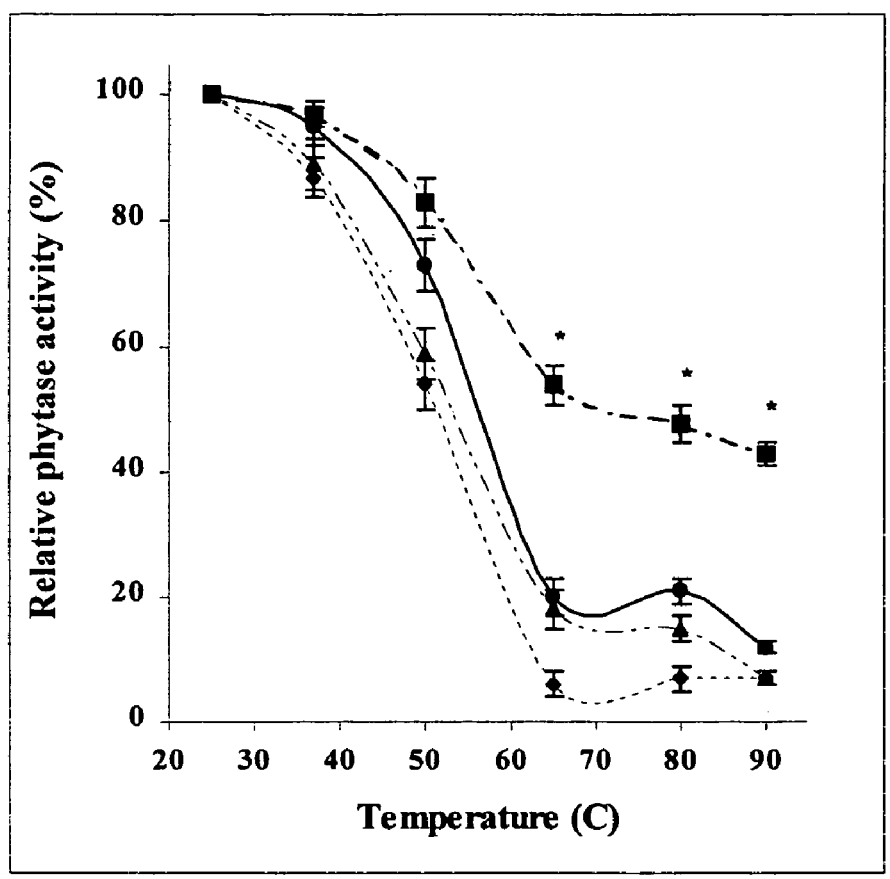
FIG. 4 shows the residual enzymatic activity of the purified r-AppA (λ) and Mutants (U, ■; Y, σ; R, ♥) after exposure for 15 min at the indicated temperature. The purified enzyme was incubated for 15 min in 0.2 M glycine-HCl, pH 2.5. At the end of heating, the reaction mixture was cooled on ice for 30 min. The initial activity with sodium phytate for each recombinant enzyme was defined as 100%. Asterisks indicate significant differences (P<0.05) between r-AppA and other mutants. Results are expressed as the mean±SE from three experiments.

Effects of Site-Directed Mutagenesis on Phytase pH and Temperature Optima and Thermostability Although Mutants R, U, and Y shared the same pH optimum (2.5) with that of r-AppA, Mutant U was more (p<0.05), while Mutant Y was less (p<0.05), active than r-AppA at the pH 3.5, 4.5, and 5.5 (FIG. 3). The temperature optimum was 65° C. for Mutant U and 55° C. for the other two mutants and r-AppA. In 0.2 M glycine-HCl, pH 2.5, Mutant U exhibited a higher (p<0.05) residual phytase activity than that of r-AppA after being heated at 80 and 90° C. for 15 min (FIG. 4).

Example 7

Effects of Site-Directed Mutagenesis on Enzyme Kinetics

The $K_m$ value for pNPP (p-nitrophenyl phosphate) was reduced by one-half and the one for sodium phytate by 70% with Mutant U, versus r-AppA (P<0.05) (Table 4). Consequently, Mutant U demonstrated a 1.9-fold increase in its apparent catalytic efficiency $k_{cat}/K_m$ for pNPP and a 5.2-fold increase for sodium phytate than that of r-AppA. Although the $k_{cat}/K_m$ values for Mutant Y were also significantly different from those of r-AppA for sodium phytate, the actual enhancement was relatively small. In contrast, Mutant R demonstrated a significantly lower catalytic efficiency than that of r-AppA for both substrates.

glycosylation of the AppA enzyme; 2) the substitutions D207N and S211N were silent; 3) the substitution C200N appeared to enhance glycosylation at other sites in the case of Mutant Y, but not in Mutant U.

In general, additional glycosylation of proteins has been shown to facilitate folding and increase stability (Haraguchi, M. et al., *Biochem. J.* 312:273–80 (1995); Imperiali, B. et

TABLE 4

Catalytic properties of r-AppA and the three mutants[1]

| | Substrate | | | | | |
|---|---|---|---|---|---|---|
| | pNPP | | | Na-Phytate | | |
| Enzyme | $K_m$ (mM) | $k_{cat}$ (min$^{-1}$) | $k_{cat}/K_m$ (min$^{-1}$M$^{-1}$) | $K_m$ (mM) | $k_{cat}$ (min$^{-1}$) | $k_{cat}/K_m$ (min$^{-1}$M$^{-1}$) |
| r-AppA | 3.66 ± 0.44 | 752 ± 7.9 | (2.0 ± 0.18) × 10$^5$ | 1.95 ± 0.25 | 2148 ± 33 | (1.11 ± 0.13) × 10$^6$ |
| R | 7.87 ± 0.84* | 390 ± 5.9* | (0.5 ± 0.07) × 10$^{5*}$ | 3.07 ± 0.26* | 1657 ± 23* | (0.54 ± 0.09) × 10$^{6*}$ |
| U | 1.86 ± 35* | 1073 ± 13* | (5.8 ± 0.37) × 10$^{5*}$ | 0.58 ± 0.08* | 4003 ± 56* | (6.90 ± 0.70) × 10$^{6*}$ |
| Y | 3.18 ± 0.39 | 787 ± 6.7 | (2.5 ± 0.17) × 10$^5$ | 2.03 ± 0.19 | 3431 ± 41* | (1.69 ± 0.21) × 10$^{6*}$ |

[1]Reaction velocity measurements were performed in triplicate as described herein. The values of $K_m$ were calculated using the Lineweaver-Burk plot method. All reactions were measured in 0.25 M glycine-HCl, pH 2.5.
*Indicates significant difference (P < 0.05) versus the r-AppA control. Results are representative of five independent experiments.

The above results indicate that additional N-glycosylation sites and/or other amino acid changes can be added to the AppA enzyme by site-directed mutagenesis. Compared with the r-AppA produced by the intact appA gene, the mutant enzymes R and Y clearly demonstrated enhanced glycosylation, as shown by their differences in molecular masses before and after deglycosylation. Thus, the engineered N-glycosylation sites in these two mutants were indeed recognized by *P. pastoris* and processed correctly. Because of the multiple mutations in Mutants R and Y, these results cannot assess the level of glycosylation at specific engineered sites, but useful information can be derived by comparisons between the mutants and r-AppA. First, although both Mutants R and Y had four additional N-glycosylation sites with respect to r-AppA, Mutant Y displayed greater than 40% more N-glycosylation than R (89% vs 48%). Because the substitution C200N in Mutant Y was the only difference between these two variants and that mutation added no additional putative N-glycosylation site, it seems that changing C200N itself might enhance N-glycosylation at certain sites. Second, although Mutant U had two additional N-glycosylation sites (Asn 207 and Asn 211), its apparent molecular weight was the same as r-AppA, suggesting the two engineered glycosylation sites in Mutant U were silent. This demonstrates that although the presence of such a signal sequence is required for glycosylation, it does not necessarily result in glycosylation (Meldgaard, M. et al., *Microbiol.* 140:159–66 (1994), which is hereby incorporated by reference). Possibly, the residues mutated in the case of Mutant U were not as solvent accessible as the structure-based sequence alignment would lead one to believe. The recently published crystal structure of the AppA enzyme may help answer this question (Lim et al., *Nat. Struct. Biol.* 7:108–13 (2000); Jia, Z. et al., *Acta Crystallogr. D Biol. Crystallogr.* 54:647–49 (1998), which are hereby incorporated by reference). Lastly, Mutant R had a significant increase in glycosylation compared with that of Mutant U. The difference might be caused by the two added N-glycosylation sites at A131N and V134N in Mutant R. Given the above results, the following observations can be made: 1) the substitutions A131N and V134N result in increased al., *Proc. Natl. Acad. Sci. USA.* 92:97–112 (1995), which are hereby incorporated by reference). Contrary to expectations, Mutants R and Y did not demonstrate enhanced thermostability, despite elevated levels of glycosylation. Surprisingly, Mutant U displayed a greater thermostability despite having the same level of glycosylation as r-AppA. Although performing C200N does not mean that N-glycosylation at other sites has occurred, greater glycosylation at specific sites is feasible. Seemingly, the mutations per se rather than glycosylation had contributed to this effect. A recent study described the production of six different phytases expressed in either *Aspergillus niger* or the yeast *Hansenula polymorpha* (Wyss, M. et al., *Appl. Environ. Microbiol.* 65:359–66 (1999), which is hereby incorporated by reference). The results indicated that levels of glycosylation depended on the host chosen, but had no significant effect on thermostability, specific activity or protein refolding (Wyss, M. et al., *Appl. Environ. Microbiol.* 65:359–66 (1999), which is hereby incorporated by reference).

The kinetic data indicate that all the three mutants and r-AppA had lower $K_m$ and higher $k_{cat}/K_m$ for sodium phytate than for pNPP. Clearly, these recombinant enzymes have higher apparent efficiency for the former than the latter, demonstrating that the AppA enzyme is more a phytase than acid phosphatase (Lim et al., *Nat. Struct. Biol.* 7:108–13 (2000); Rodriguez, E. et al., *Biochem. Biophys. Res. Commun.* 257:117–23 (1999), which are hereby incorporated by reference). Mutant U exhibited the largest enhancement in its apparent efficiency for both substrates over that of r-AppA. The enhancement in $k_{cat}/K_m$ is most likely due to a large decrease in $K_m$ (1.86 vs 3.66 mM for pNPP and 0.58 vs 1.95 mM for sodium phytate). This means that the Mutant U is saturated at a much lower concentration of substrate than r-AppA. In addition, there was also a significant difference in $k_{cat}$ for both substrates between these two forms of phytase. Based on the structure of rat acid phosphatase (Schneider, G. et al., *EMBO J.* 12:2609–15 (1993), which is hereby incorporated by reference), these mutations do not seem to be involved in the enzyme active site or the formation of acid phosphatase dimer. Probably, these mutations singly or jointly affect the conformational flexibility of the enzyme, such as described previously for another protein (Kern, G. et al., *Protein Sci.* 2:1862–68 (1993), which is hereby incorporated by reference). Based on the recently solved crystal structures of *E. coli* phytase (Lim et al., *Nat. Struct. Biol.* 7:108–13 (2000); Jia, Z. et al., *Acta Crystallogr. D Biol. Crystallogr.* 54:647–49 (1998), which are hereby incorporated by reference), none of these mutations are directly involved in the substrate-binding pocket. However, C200 and C210, labeled as C178 and C188 by Lim et al. (Lim et al., *Nat. Struct. Biol.* 7:108–13 (2000), which is hereby incorporated by reference), are involved in a disulfide bond between helix G and the GH loop in the α-domain of the protein (Lim et al., *Nat. Struct. Biol.* 7:108–13 (2000), which is hereby incorporated by reference). With the mutation C200N, the unique disulfide bond into the α-domain is no longer present in the GH loop. This change may result in a better flexibility of the α-domain toward the central cavity or "substrate-binding site" of the enzyme (Lim et al., *Nat. Struct. Biol.* 7:108–13 (2000), which is hereby incorporated by reference). This internal flexibility may be also supported by the fact that Mutant U, and to a lesser extent Mutant Y, demonstrated improvement in the catalytic efficiency for sodium phytate hydrolysis. Since there was no enhanced glycosylation for Mutant U, engineered glycosylation sites N207 and N211, labeled as D185 and S189 by Lim et al. (Lim et al., *Nat. Struct. Biol.* 7:108–13 (2000), which is hereby incorporated by reference), may be masked from the exposed surface. The improvement of thermostability for Mutant U may be therefore explained by an increasing number of hydrophobic interactions not presented in Mutant Y or Mutant R.

It is worth mentioning that the specific activities of phytase in all the three mutants and r-AppA were not significantly affected by deglycosylation. However, deglycosylation, as shown in glycoprotein hormones (Terashima, M. et al., *Eur. J. Biochem.* 226:249–54 (1994), which is hereby incorporated by reference) or the *Schwanniomyces occidentalis* α-amylase expressed in *S. cerevisiae* (Han, Y. et al., *Appl. Environ. Microbiol.* 65:1915–18 (1999), which is hereby incorporated by reference), may be associated with possible conformational changes that modulate the substrate binding and (or) the velocity of its utilization. All of the mutants and the intact control were completely inactivated by both β-mercaptoethanol and deglycosylation treatments. This suggests that the four disulfide bonds play altogether a key role in maintaining catalyic function of these recombinant phytases (Ullah, A. H. J. et al., *Biochem. Biophys. Res. Commun.* 227:311–17 (1996), which is hereby incorporated by reference).

In conclusion, when the G helix and the GH loop do not contain the disulfide bond C200/C210 in Mutant U, the α-domain may become slightly more flexible, resulting in a positive modulation on the catalytic efficiency and the thermostability of the enzyme. Because the *E. coli* phytase crystal structure will be released in the near future (Lim et al., *Nat. Struct. Biol.* 7:108–13 (2000), which is hereby incorporated by reference), more targeted mutagenesis studies should shed light on conformational changes that may improve the properties of the enzyme.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated mutant phytase produced by making a plurality of amino acid substitutions in a wild-type *Escherichia coli* phytase having an amino acid sequence of SEQ ID NO: 1, said amino acid substitutions comprising substitutions at positions 200, 207, and 211, wherein the mutant phytase is encoded by a nucleic acid molecule that comprises a nucleotide sequence of SEQ ID NO:4 or that hybridizes to the complement of the nucleotide sequence of SEQ ID NO:4 under stringency conditions comprising hybridization at 42° C. in a hybridization medium comprising 5X SSPE and 50 percent formamide with washing at 65° C. with 0.5X SSPE, and wherein the mutant phytase has phytase activity.

2. The isolated mutant phytase according to claim 1, wherein the amino acid substitution at position 200 is an asparagine amino acid residue for a cysteine amino acid residue, the amino acid substitution at position 207 is an asparagine amino acid residue for an aspartate amino acid residue, and the amino acid substitution at position 211 is an asparagine amino acid residue for a serine amino acid residue, said isolated mutant phytase having an amino acid sequence of SEQ ID NO:3.

3. The isolated mutant phytase according to claim 1, wherein the isolated mutant phytase is in purified form.

4. The isolated mutant phytase according to claim 1, wherein the isolated mutant phytase is recombinant.

5. An isolated mutant phytase which differs from a wild-type *Escherichia coli* phytase having an amino acid sequence of SEQ ID NO: 1 by at least one amino acid substitution which comprises a substitution of a cysteine amino acid residue with a non-cysteine amino acid residue at at least one of positions 200 or 210, wherein the mutant phytase is encoded by a nucleic acid molecule that hybridizes to the nucleotide sequence of SEQ ID NO:2 under stringency conditions comprising hybridization at 42° C. in a hybridization medium comprising 5X SSPE and 50 percent formamide with washing at 65° C. with 0.5X SSPE, and wherein the mutant phytase has phytase activity.

6. The isolated mutant phytase according to claim 5, wherein the isolated mutant phytase is in purified form.

7. The isolated mutant phytase according to claim 5, wherein the isolated mutant phytase is recombinant.

8. An isolated mutant phytase encoded by a nucleic acid molecule comprising a nucleotide sequence having greater than 95 percent homology to the nucleotide sequence of SEQ ID NO:2, and wherein the mutant phytase is produced by introducing at least one amino acid substitution into a wild-type phytase having an amino acid sequence of SEQ ID NO:1, wherein said introducing comprises replacing a cysteine amino acid residue with a non-cysteine amino acid residue, and wherein said at least one amino acid substitution disrupts at least one disulfide bond of the wild-type phytase.

9. The isolated mutant phytase according to claim 8, wherein the isolated mutant phytase is in purified form.

10. The isolated mutant phytase according to claim 8, wherein the isolated mutant phytase is recombinant.

* * * * *